US006737422B2

(12) United States Patent
McNaughton-Smith et al.

(10) Patent No.: US 6,737,422 B2
(45) Date of Patent: May 18, 2004

(54) BENZANILIDES AS POTASSIUM CHANNEL OPENERS

(75) Inventors: Grant A. McNaughton-Smith, Morrisville, NC (US); Michael F. Gross, Durham, NC (US); Alan D. Wickenden, Cary, NC (US)

(73) Assignee: ICAgen, Inc., Durham, NC (US)

( * ) Notice: Subject to any disclaimer, the term of this patent is extended or adjusted under 35 U.S.C. 154(b) by 174 days.

(21) Appl. No.: 10/004,122

(22) Filed: Nov. 1, 2001

(65) Prior Publication Data

US 2002/0091122 A1 Jul. 11, 2002

Related U.S. Application Data

(62) Division of application No. 09/632,576, filed on Aug. 4, 2000, now Pat. No. 6,372,767.
(60) Provisional application No. 60/147,221, filed on Aug. 4, 1999.

(51) Int. Cl.[7] ...................... A61K 31/44; C07D 401/02; C07D 213/02

(52) U.S. Cl. ................ 514/235.5; 514/255.05; 514/256; 514/332; 514/336; 514/341; 514/343; 514/352; 544/124; 544/333; 544/405; 546/272.7; 546/276.4; 546/253.4; 546/309; 546/255

(58) Field of Search .................. 546/809, 255, 546/272.7, 276.4, 283.4; 514/352, 235.5, 255.05, 256, 332, 336, 341, 343; 544/124, 333, 405

(56) References Cited

FOREIGN PATENT DOCUMENTS

| JP | 58-069812 A2 | 4/1983 |
| JP | 181257 A2 | 10/1984 |
| WO | WO 98/42672 A1 | 10/1998 |
| WO | WO 99/05113 | 2/1999 |

*Primary Examiner*—Zinna Northington Davis
(74) *Attorney, Agent, or Firm*—Townsend and Townsend and Crew LLP

(57) ABSTRACT

Benzanilides are provided which are voltage-dependent potassium channel openers. Methods of using the benzanilides of the invention are also provided.

59 Claims, 6 Drawing Sheets

(64)

(65)

(66)

(67)

(68)

(69)

(70)

(71)

(72)

(73)

(74)

(75)

(76)

(77)

(78)

(79)

(80)

(81)

(82)

(83)

(84)

(85)

(86)

(87)

ns application is a divisional of and claims the benefit
BENZANILIDES AS POTASSIUM CHANNEL OPENERS

CROSS-REFERENCES TO RELATED APPLICATIONS

This application is a divisional of and claims the benefit of U.S. application Ser. No. 09/632,576, filed Aug. 4, 2000, now U.S. Pat. No. 6,372,767 which claims the benefit of U.S. Provisional Application No. 60/147,221, filed Aug. 4, 1999, the disclosures of each which are incorporated herein by reference, in their entirety for all purposes.

FIELD OF THE INVENTION

This invention relates to the use of benzanilides as potassium channel openers and to the treatment of diseases modulated by potassium channel opening. Additionally, this invention relates to novel compounds that are useful as potassium channel openers.

BACKGROUND OF THE INVENTION

Ion channels are cellular proteins that regulate the flow of ions, including calcium, potassium, sodium and chloride, into and out of cells. These channels are present in all human cells and affect such processes as nerve transmission, muscle contraction and cellular secretion. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels have now been associated with a number of physiological processes, including regulation of heartbeat, dilation of arteries, release of insulin, excitability of nerve cells, and regulation of renal electrolyte transport.

Potassium channels are made by alpha subunits that fall into at least 8 families, based on predicted structural and functional similarities (Wei et al., *Neuropharmacology* 35(7) :805–829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25):14066–71 (1997)) and are gated by both voltage and calcium or pH (Schreiber et al., *J. Biol. Chem.* 273:3509–16 (1998)). Another family, the inward rectifier potassium channels (Kir), belong to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493:625–633 (1996); Shi et al., *Neuron* 16(4):843–852 (1996)). In another example, the KQT family beta subunit, minK, primarily changes activation kinetics (Sanguinetti et al, *Nature* 384:80–83 (1996)).

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 (Butler et al., *Science* 261:221–224 (1993); Schreiber et al., *J. Biol. Chem.*, 273:3509–16 (1998); and Joiner et al., *Nature Neurosci.* 1: 462–469 (1998)). These Slo family members have been shown to be voltage and/or calcium gated, and/or regulated by intracellular pH.

Certain members of the Kv family of potassium channels were recently renamed (see Biervert, et al., *Science* 279:403–406 (1998)). KvLQT1 was re-named KCNQ1, and the KvLQT1-related channels (KvLR1 and KvLR2) were renamed KCNQ2 and KCNQ3, respectively. More recently, a fourth member of the KCNQ subfamily was identified (KCNQ4) as a channel expressed in sensory outer hair cells (Kubisch, et al., *Cell* 96(3):437–446 (1999)).

KCNQ2 and KCNQ3 have been shown to be nervous system-specific potassium channels associated with benign familial neonatal convulsions ("BFNC"), a class of idiopathic generalized epilepsy (see, Leppert, et al., *Nature* 337:647–648 (1989)). These channels have been linked to M-current channels (see Wang, et al., *Science* 282:1890–1893 (1998)). The discovery and characterization of these channels and currents provides useful insights into how these voltage dependent (Kv) potassium channels function in different environments, and how they respond to various activation mechanisms. Such information has now led to the identification of modulators of KCNQ2 and KCNQ3 potassium channels or the M-current, and the use of such modulators as therapeutic agents. The modulators are the subject of the present invention.

Bioactive compounds based on a benzanilide motif are known for the treatment of circulatory disturbances (Arita et al., U.S. Pat. No. 5,958,944), fungal infections (Baker et al., U.S. Pat. No. 4,845,107), inflammation (Beeley et al, U.S. Pat. No. 5,340,827) and ulcers and bacterial infections (Nishino et al., U.S. Pat. No. 5,859,032). The previous benzanilides do not include the 2-substituted-5-aminopyridine substructure found in the compounds of the present invention. Moreover, none of the known benzanilide analogues are disclosed to modulate potassium channels or to be of use in treating conditions involving the modulation of potassium channels.

SUMMARY OF THE INVENTION

The present invention provides compounds which are useful in the treatment of diseases through the modulation of potassium ion flux through voltage-dependent potassium channels. More particularly, the invention provides compounds, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases, and as neuroprotective agents (e.g., to prevent stroke and the like)).

In one aspect, the present invention provides compounds having a structure according to Formula I:

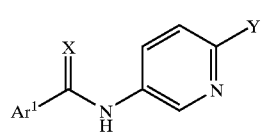

(I)

in which the symbol $Ar^1$ represents a member selected from the group consisting of aryl, substituted aryl, heteroaryl and substituted heteroaryl. The letter X represents a member selected from the group consisting of O, S and N—$R^1$, in which $R^1$ is H, $(C_1-C_8)$alkyl, substituted $(C_1-C_8)$alkyl, heteroalkyl, substituted heteroalkyl, aryl, substituted aryl, heteroaryl, substituted heteroaryl, aryl$(C_1-C_4)$alkyl, substituted aryl$(C_1-C_4)$alkyl, CN, —C(O)$R^2$, —O$R^3$, —C(O)N$R^3R^4$, or —S(O)$_2$N$R^3R^4$. The symbol $R^2$ represents a member selected from the group consisting of $(C_1-C_8)$alkyl, substituted $(C_1-C_8)$alkyl, cycloalkyl, substituted cycloalkyl, heteroalkyl, substituted heteroalkyl, heterocyclyl, substituted heterocyclyl, substituted aryl, heteroaryl, substituted heteroaryl, aryl$(C_1-C_4)$alkyl and substituted aryl$(C_1-C_4)$ alkyl. $R^3$ and $R^4$ are each members independently selected from the group consisting of hydrogen, $(C_1-C_8)$alkyl, substituted $(C_1-C_8)$alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl$(C_1-C_4)$alkyl and substituted aryl $(C_1-C_4)$alkyl. Alternatively, $R^3$ and $R^4$ can be combined with the nitrogen to which each is attached to form a 5-, 6- or 7-membered ring, optionally having additional heteroatoms at the ring vertices. The letter Y represents a member selected from the group consisting of halogen, $C_1-C_4$ alkyl, $C_1-C_4$ substituted alkyl, —OCH$_3$ and —OCF$_3$.

In another aspect, the present invention provides pharmaceutical compositions comprising a pharmaceutically acceptable excipient and a compound having a structure according to Formula II:

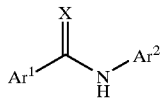

(II)

in which the symbols $Ar^1$ and $Ar^2$ independently represent aryl, substituted aryl, heteroaryl and substituted heteroaryl. The letter represents O, S or N—$R^1$, in which $R^1$ is a H, $(C_1-C_8)$alkyl, substituted $(C_1-C_8)$alkyl, aryl, substituted aryl, heteroaryl, substituted heteroaryl, aryl$(C_1-C_4)$alkyl, substituted aryl$(C_1-C_4)$alkyl, CN, —C(O)R, —OR$^3$, —C(O)N$R^3R^4$, or —S(O)$_2$N$R^3R^4$. The symbol $R^2$ represents $(C_1-C_8)$alkyl, substituted $(C_1-C_8)$alkyl, aryl, substituted aryl, heteroaryl, substituted heteroaryl, aryl$(C_1-C_4)$ alkyl or substituted aryl$(C_1-C_4)$alkyl. $R^3$ and $R^4$ are each members independently selected from the group consisting of hydrogen, $(C_1-C_8)$alkyl, substituted $(C_1-C_8)$alkyl, aryl, substituted aryl, heteroaryl, substituted heteroaryl, aryl $(C_1-C_4)$alkyl and substituted aryl$(C_1-C_4)$alkyl. Alternatively, $R^3$ and $R^4$ can be combined with the nitrogen to which each is attached to form a 5-, 6- or 7-membered ring optionally having additional heteroatoms at the ring vertices.

In yet another aspect, the present invention provides a method for modulating ion flux through voltage dependent potassium channels, comprising contacting a cell containing the target ion channels with a compound according to Formula II, above.

In still another aspect, the present invention provides a method for the treatment of diseases through modulation of ion flux through voltage dependent potassium channels, the method comprising treating the host with an effective amount of a potassium channel compound of Formula II, above.

DETAILED DESCRIPTION OF THE INVENTION AND THE PREFERRED EMBODIMENTS

Abbreviations and Definitions

Figure 1:
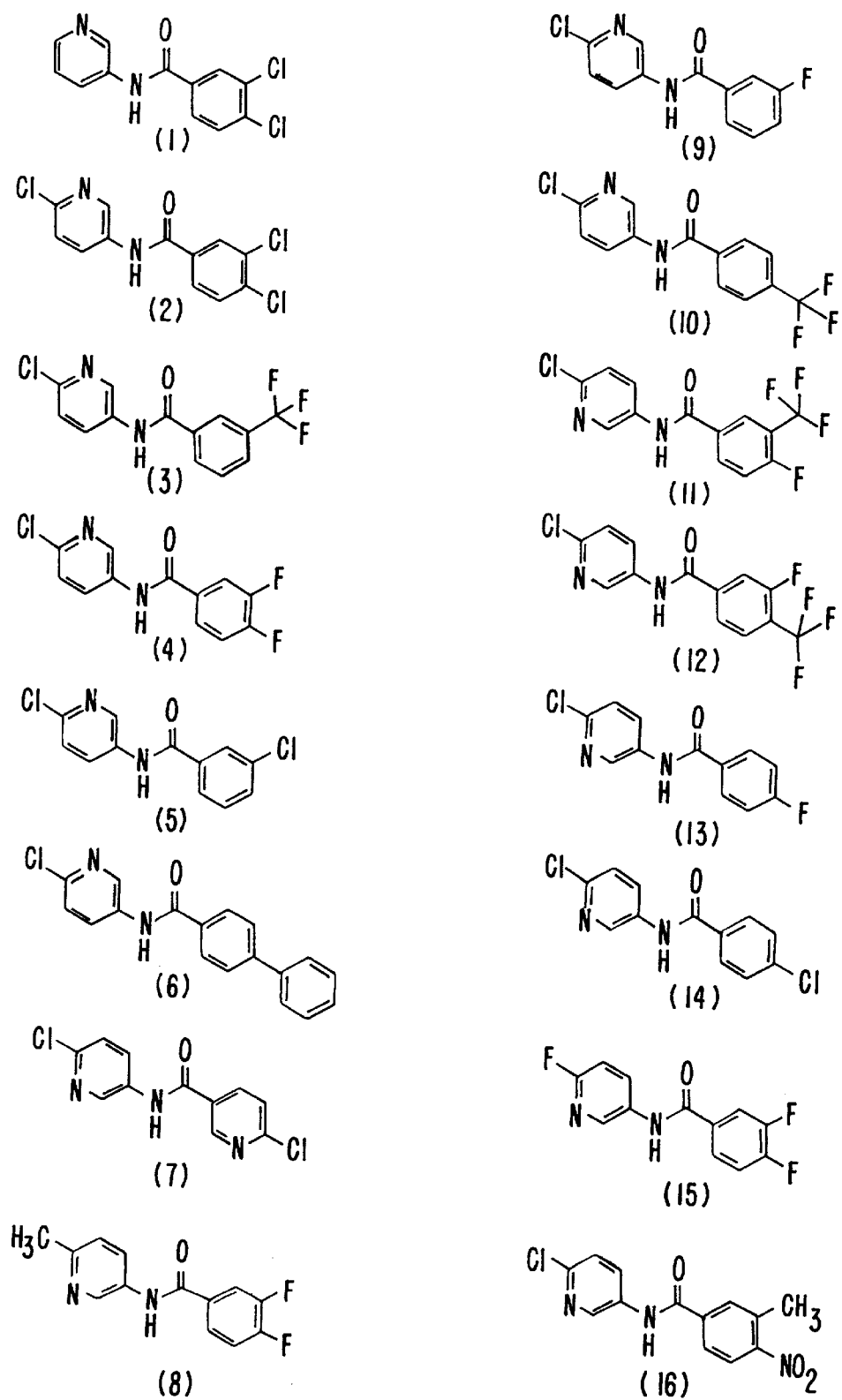
FIG. 1 is a tabulation of 100 representative compounds of the invention.
Figure 1:
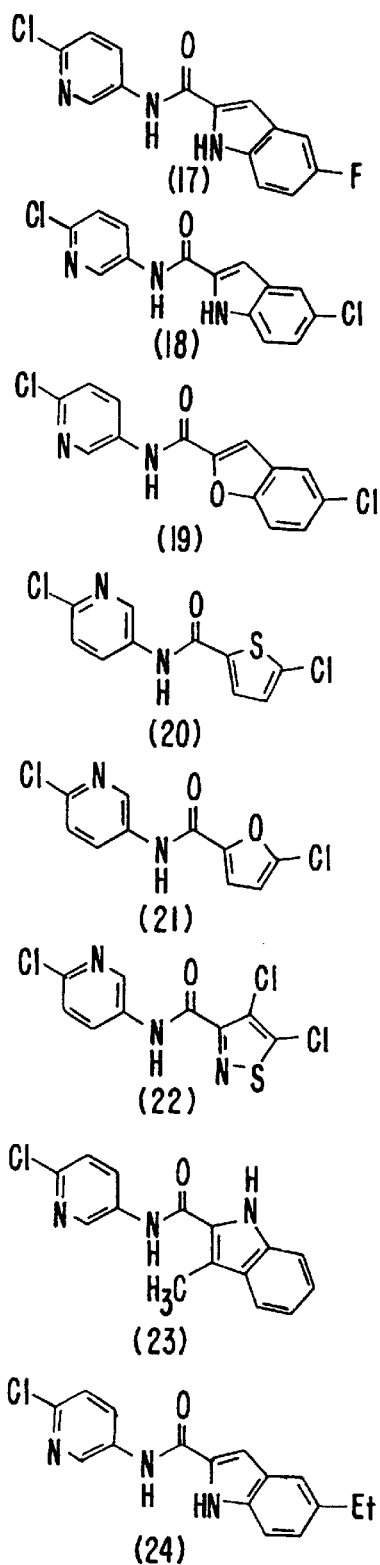
Figure 1:
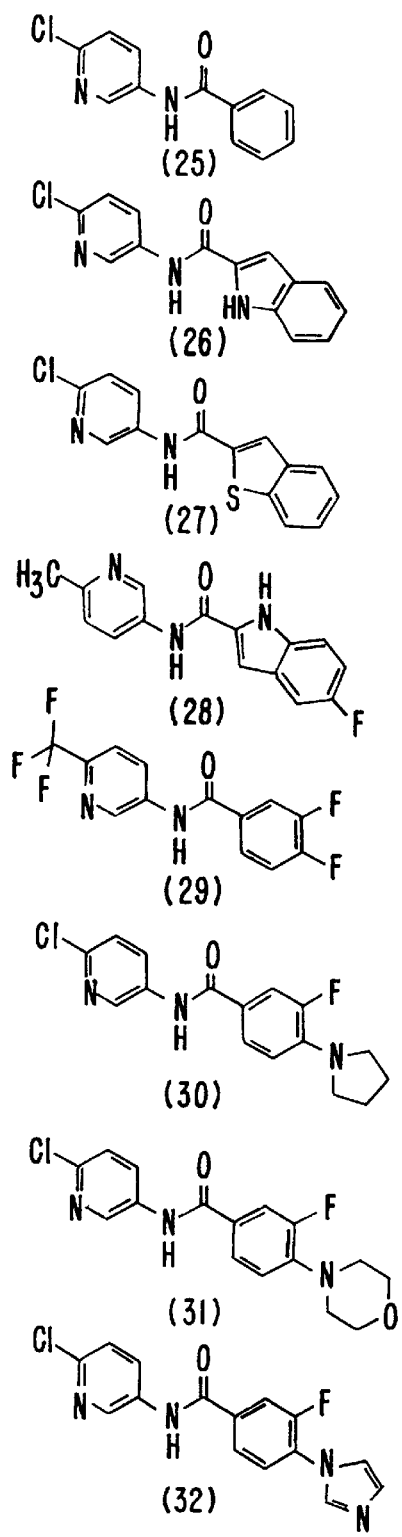
Figure 1:
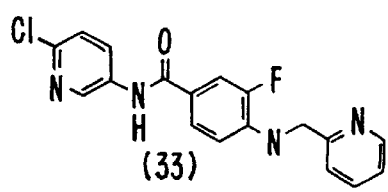
Figure 1:
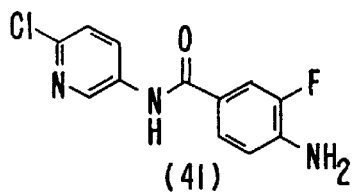
Figure 1:
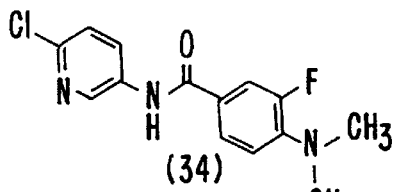
Figure 1:
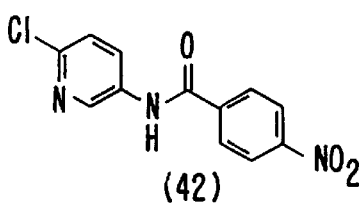
Figure 1:
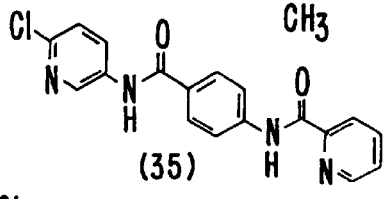
Figure 1:
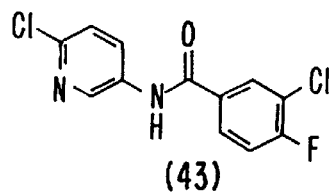
Figure 1:
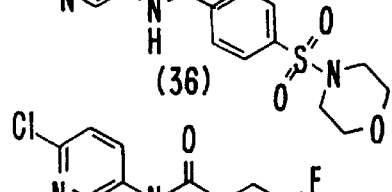
Figure 1:
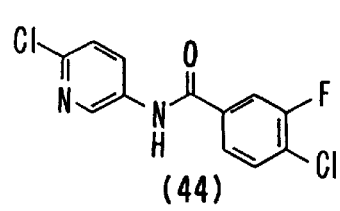
Figure 1:
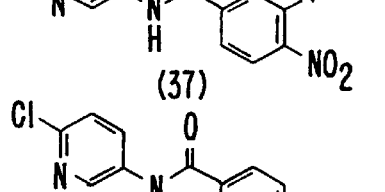
Figure 1:
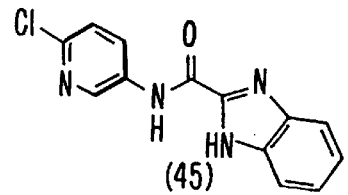
Figure 1:
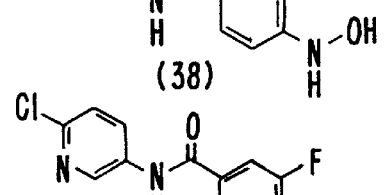
Figure 1:
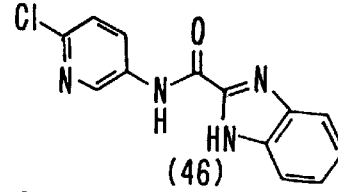
Figure 1:
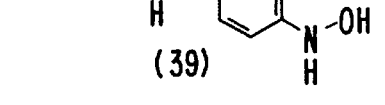
Figure 1:
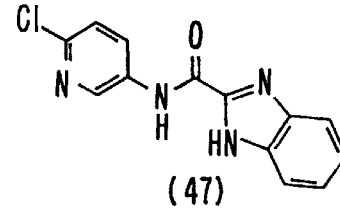
Figure 1:
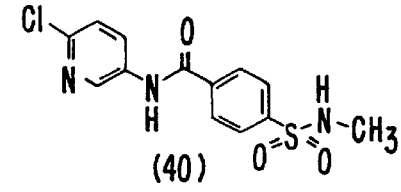
Figure 1:
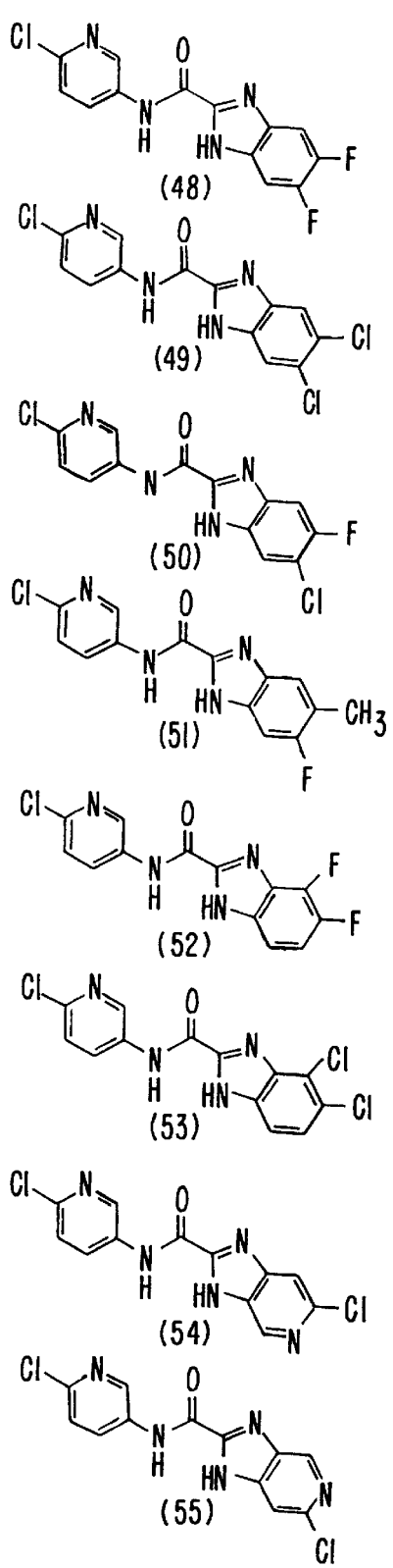
Figure 1:
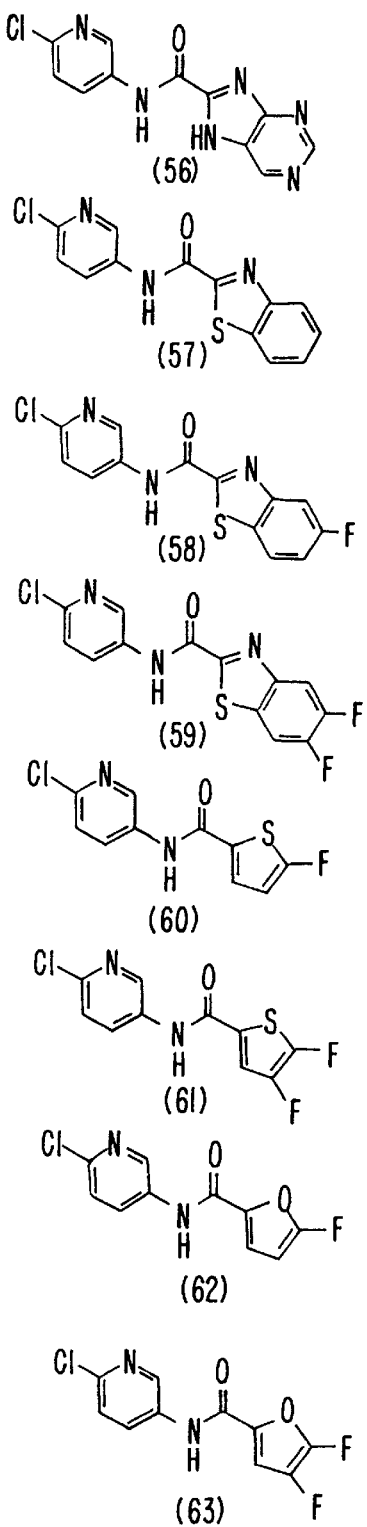
Figure 1:
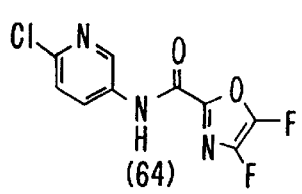
Figure 1:
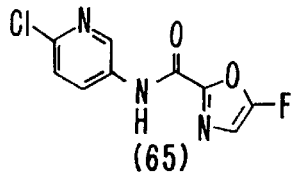
Figure 1:
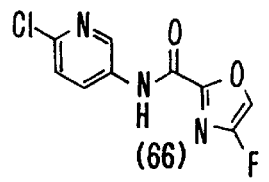
Figure 1:
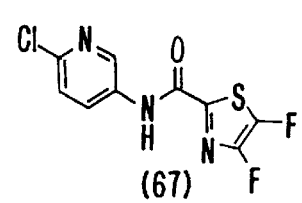
Figure 1:
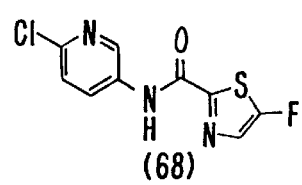
Figure 1:
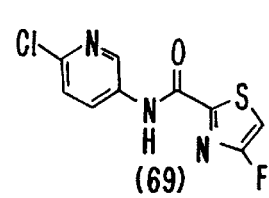
Figure 1:
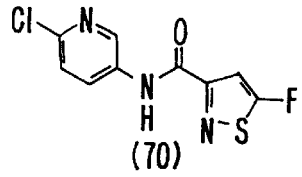
Figure 1:
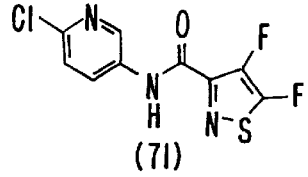
Figure 1:
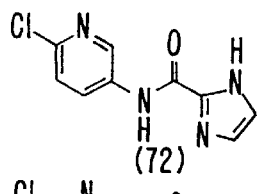
Figure 1:
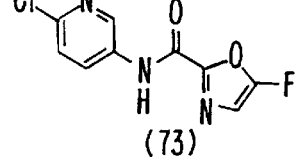
Figure 1:
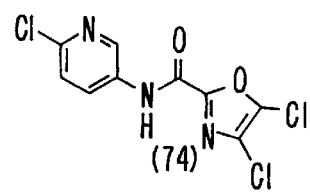
Figure 1:
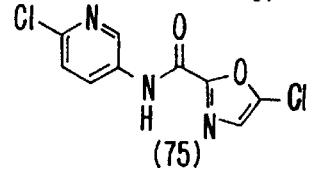
Figure 1:
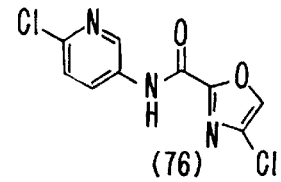
Figure 1:
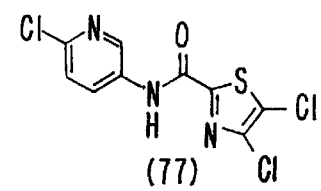
Figure 1:
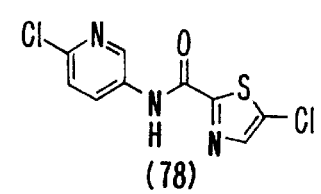
Figure 1:
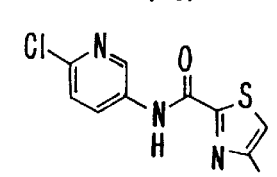
Figure 1:
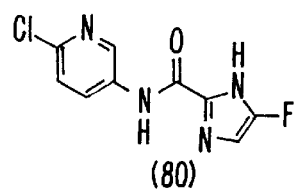
Figure 1:
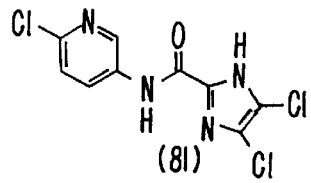
Figure 1:
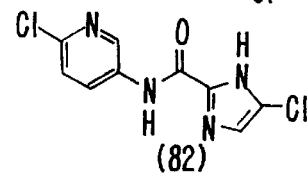
Figure 1:
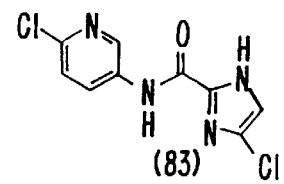
Figure 1:
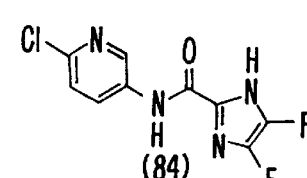
Figure 1:
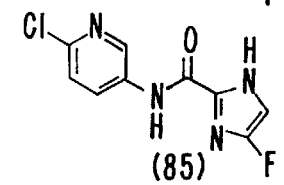
Figure 1:
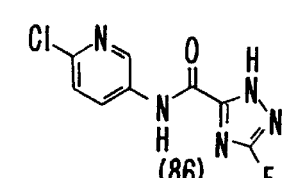
Figure 1:
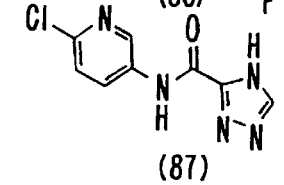
Figure 1:
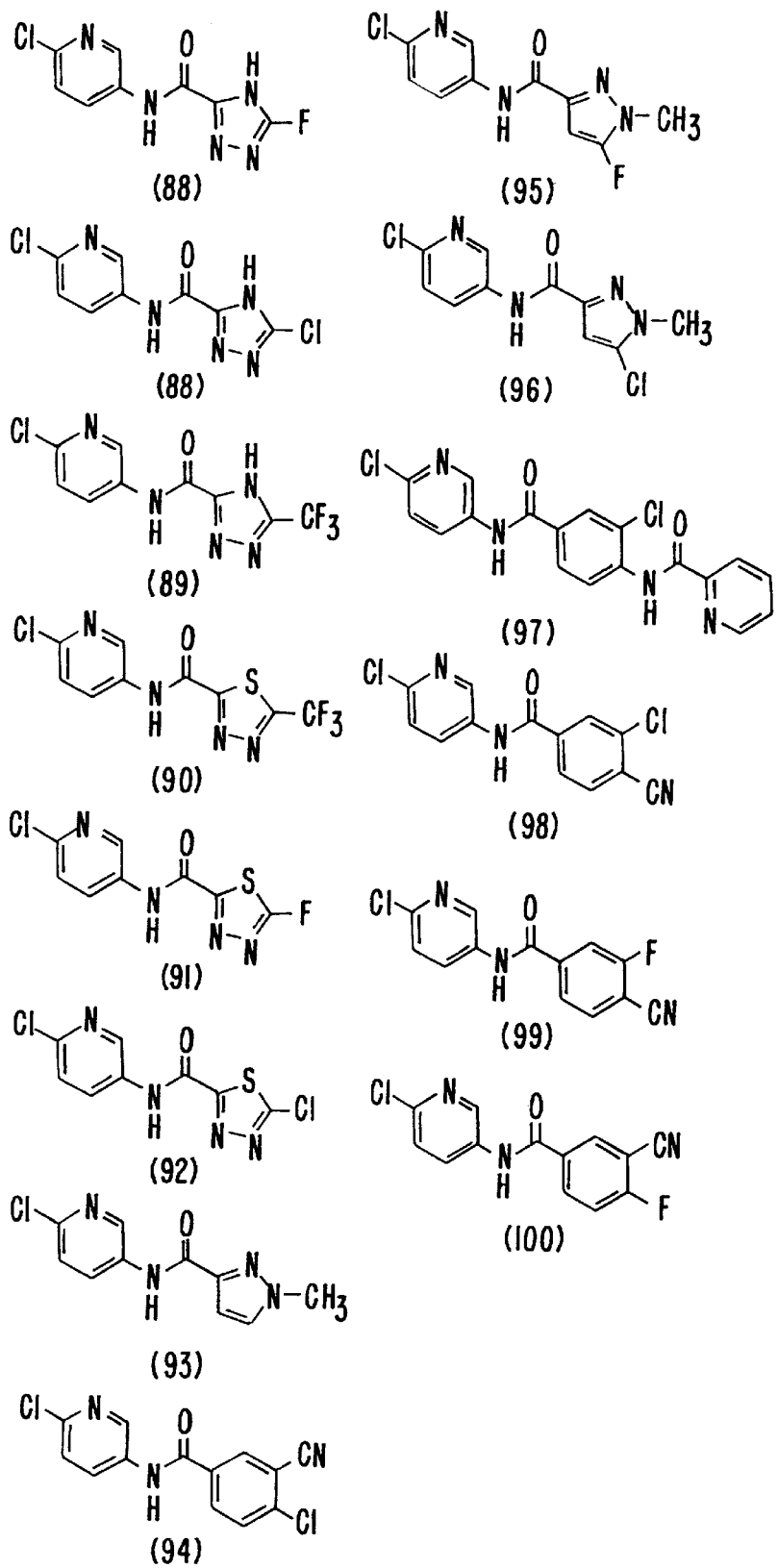

The abbreviations used herein have their conventional meaning within the chemical and biological arts. For example: CHO, Chinese hampster ovary; EBSS, Earl's Balanced Salt Solution; KCNQ, potassium channel Q; KCNQ2, potassium channel Q2; SDS, sodium dodecyl sulfate; Et$_3$N: triethylamine; MeOH: methanol; and DMSO: dimethylsulfoxide.

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quatemized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$–$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from, for example: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2m'+1), where m' is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. Thus, —NR'R" is meant to include, for example, 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl and heteroaryl groups are varied and are selected from, for example: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R" and R'" are independently selected from, for example, hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

The development of therapeutic agents, which act on potassium ion channels, has received considerable recent attention. One group has described a family of N-alkyl benzamides that act by blocking $I_{Ks}$ potassium channels (see PCT/US98/02364, published as WO 98/37068). Surprisingly, the N-aryl benzamides and related compounds provided herein, act by opening the KCNQ potassium channels.

In view of the above-noted discovery, the present invention provides compounds, compositions, and methods for increasing ion flux in voltage-dependent potassium channels, particularly those channels responsible for the M-current. As used herein, the term "M-current," "channels responsible for the M-current" and the like, refers to a slowly activating, non-inactivating, slowly deactivating voltage-gated K$^+$ channel. M-current is active at voltages close to the threshold for action potential generation in a wide variety of neuronal cells, and thus, is an important regulator of neuronal excitability.

Recently, members of the voltage-dependent potassium channel family have been shown to be directly involved in diseases of the central or peripheral nervous system. The benzanilides provided herein are now shown to act as KCNQ channel openers, particularly for KCNQ2 and KCNQ3, as well as the heteromultimer channels such as KCNQ2/3 or the M-current.

Description of the Embodiments

I. Modulators of Voltage-dependent Potassium Channels

In view of the above surprising discovery, the present invention provides in one aspect, compounds according to Formula I:

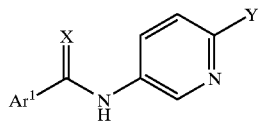
(I)

in which the symbol $Ar^1$ represents a member selected from the group consisting of aryl, substituted aryl, heteroaryl and substituted heteroaryl. The letter X represents a member selected from the group consisting of O, S and N—$R^1$, in which $R^1$ is H, ($C_1$–$C_8$)alkyl, substituted ($C_1$–$C_8$)alkyl, heteroalkyl, substituted heteroalkyl, aryl, substituted aryl, heteroaryl, substituted heteroaryl, aryl($C_1$–$C_4$)alkyl, substituted aryl($C_1$–$C_4$)alkyl, CN, —C(O)$R^2$, —O$R^3$, —C(O)N$R^3R^4$, or —S(O)$_2$N$R^3R^4$. The symbol $R^2$ represents a member selected from the group consisting of ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, substituted aryl, heteroaryl, substituted heteroaryl, aryl($C_1$–$C_4$)alkyl and substituted aryl($C_1$–$C_4$) alkyl. $R^3$ and $R^4$ are each members independently selected from the group consisting of hydrogen, ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl ($C_1$–$C_4$)alkyl. Alternatively, $R^3$ and $R^4$ can be combined with the nitrogen to which each is attached to form a 5-, 6- or 7-membered ring, optionally having additional heteroatoms at the ring vertices. The letter Y represents a member selected from the group consisting of halogen, $C_1$–$C_4$ alkyl, $C_1$–$C_4$ substituted alkyl, —OCH$_3$ and —OCF$_3$.

In one group of preferred embodiments, $Ar^1$ phenyl, substituted phenyl, indolyl, substituted indolyl, benzofuranyl, substituted benzofuranyl, furanyl, substituted furanyl, thienyl, substituted thienyl, isothiazolyl, substituted isothiazolyl, pyrazolyl or substituted pyrazolyl. Still further preferred are those embodiments in which $Ar^1$ is substituted phenyl, substituted or unsubstituted 2-indolyl and substituted or unsubstituted 2-thienyl. In yet another group of preferred embodiments, X is O.

In those preferred embodiments, in which $Ar^1$ is substituted, the $Ar^1$ substituents are halogen, alkyl, halo ($C_1$–$C_4$)alkyl, ($C_1$–$C_4$)alkoxy, halo($C_1$–$C_4$)alkoxy, nitro, cyano, —N $R^7$C(O) $R^8$, —N $R^7R^8$, phenyl and/or substituted phenyl. The symbols $R^7$ and $R^8$ independently represent hydrogen, ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$) alkyl and substituted aryl($C_1$–$C_4$)alkyl. Alternatively, $R^7$ and $R^8$ are combined with the nitrogen to which it is attached to form a 5-, 6- or 7-membered ring, optionally having additional heteroatoms at the ring vertices.

In yet a further group of preferred embodiments, the compounds of the invention have a structure according to Formula III:

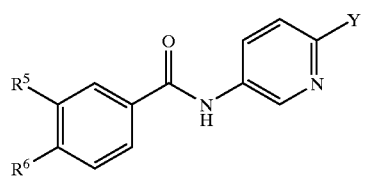
(III)

in which the symbols $R^5$ and $R^6$ independently represent H, halogen, alkyl, halo($C_1$–$C_4$)alkyl, nitro, cyano or phenyl, with the proviso that both $R^5$ and $R^6$ are not H. In a still further group of preferred embodiments, the symbols $R^5$ and $R^6$ independently represent H, F, and Cl.

Certain combinations of the above preferred embodiments form a group of particularly preferred compounds. Accordingly, one certain preferred compounds of the present invention are those set forth in FIG. 1, appended hereto.

Also within the scope of the present invention are compounds of the invention that function as poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or reactive analogues thereof are attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Preparation of Potassium Channel Openers

Compounds of the present invention can be prepared using readily available starting materials or known intermediates. Briefly, the synthesis of N-aryl benzamides involves formation of a single amide bond from a "carbonyl component" (typically a carboxylic acid, carboxylic acid chloride, ester or an activated form of a carboxylic acid, for example, a symmetrical or mixed anhydride) and an "amine component" (typically, an aniline, aniline derivative, amino heterocycle, and the like). General and specific procedures for the preparation of the present compounds are provided in the examples below.

Other compounds of the present invention can be prepared using standard procedures as outlined in Scheme 1 below. In this scheme, an N-phenyl benzamide (i, wherein $Y^1$ and $Y^2$ represent substituents, including multiple substituents on the aryl groups) can be treated with reagents such as Lawessons's reagent to provide the thioamides, ii. Alkylation of ii, with, for example, methyl iodide produces iii which can be converted to target structures iv, v and vi. Thus, treatment of iii with sodium hydride (or another suitable base) and sulfamide provides the sulfamoylimino derivative, iv. Similarly, treatment of iii with sodium hydride or another base, followed by cyanamide provides v. Conversion of v to vi can be accomplished with HCl.

One of skill in the art will recognize that other compounds of the present invention can be prepared from intermediates such as iii. For example, treatment of iii with a primary or secondary amine will provide amidine derivatives that are useful as described or they can be further derivatized.

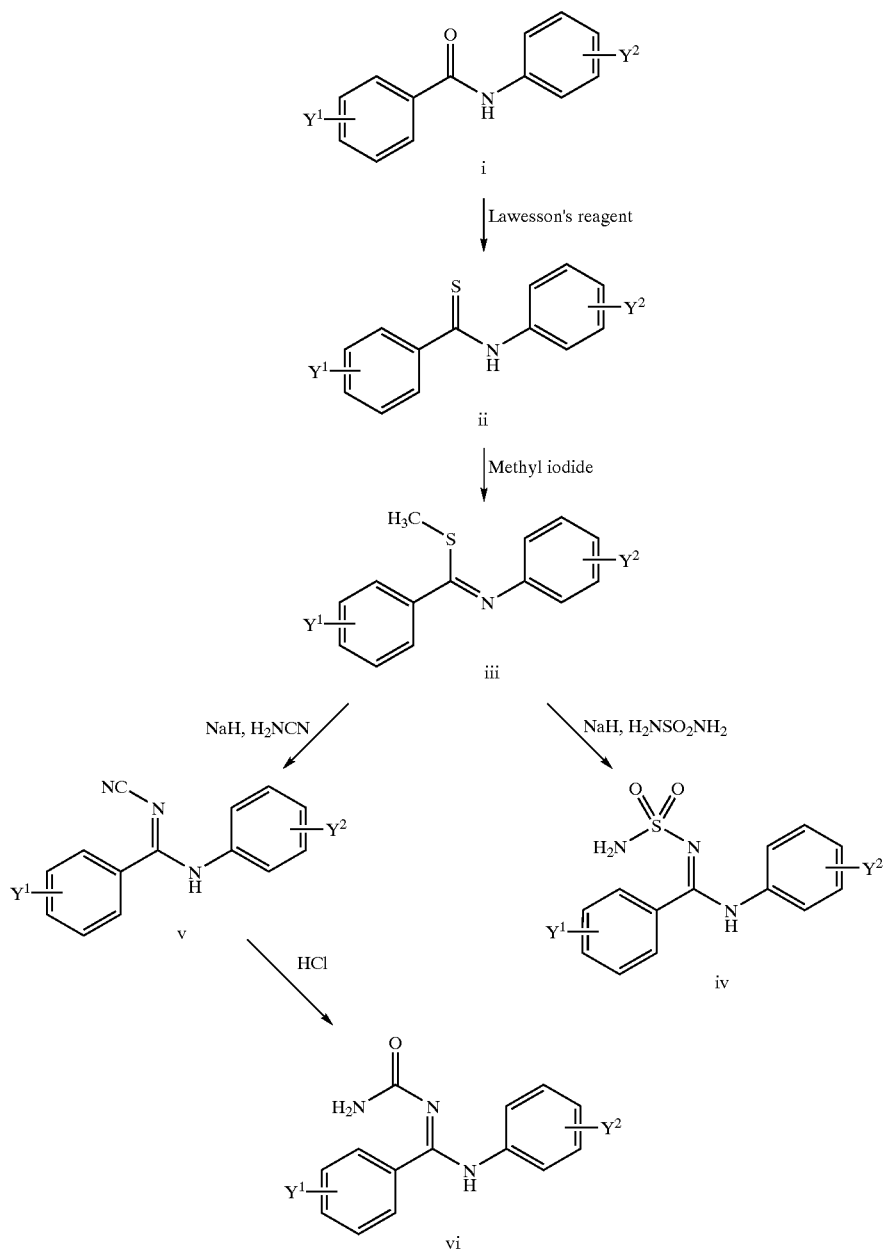

SCHEME 1

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyvalent framework and a compound of the invention. If it is desired to prepare a hetereofuntionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

II. Assays for Modulators of KCNQ Channels

KCNQ monomers as well as KCNQ alleles and polymorphic variants are subunits of potassium channels. The activity of a potassium channel comprising KCNQ subunits can be assessed using a variety of in vitro and in vivo assays, e.g., measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for inhibitors and activators of channels comprising KCNQ. Such modulators of a potassium channel are useful for treating various disorders involving potassium channels, including but not limited to, for example, central and peripheral nervous system disorders (e.g., migraine, ataxia, Parkinson's disease, bipolar disorders, spasticity, mood disorders, brain tumors, psychotic disorders, myokymia, seizures, epilepsy, hearing and vision loss, Alzheimer's disease, age-related memory loss, learning deficiencies, and motor neuron diseases, and can also be used as neuroprotective agents (e.g., to prevent stroke and the like). Such modulators are also useful for investigation of the channel diversity provided by KCNQ and the regulation/modulation of potassium channel activity provided by KCNQ.

Modulators of the potassium channels are tested using biologically active KCNQ, either recombinant or naturally occurring, or by using native cells, like cells from the nervous system expressing the M-current. KCNQ can be isolated, co-expressed or expressed in a cell, or expressed in a membrane derived from a cell. In such assays, KCNQ2 is expressed alone to form a homomeric potassium channel or is co-expressed with a second subunit (e.g., another KCNQ family member, preferably KCNQ3) so as to form a heteromeric potassium channel. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Activation of channels comprising KCNQ2 is achieved when the potassium channel activity value relative to the control is 110%, more preferably 130%, more preferably 170% higher. Compounds that increase the flux of ions will cause a detectable increase in the ion current density by increasing the probability of a channel comprising KCNQ2 being open, by decreasing the probability of it being closed, by increasing conductance through the channel, and increasing the number or expression of channels.

Changes in ion flux may be assessed by determining changes in polarization (i.e., electrical potential) of the cell or membrane expressing the potassium channel comprising KCNQ2, KCNQ2/3 or the M-current. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336:1575–1595 (1997)). Whole cell currents are conveniently determined using the standard methodology (see, e.g., Hamil et al., *Pflugers. Archiv.* 391:85 (1981). Other known assays include: radiolabeled rubidium flux assays and fluorescence assays using voltage-sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing potassium flux through the channel proteins comprising KCNQ2 or heteromultimers of KCNQ subunits can be performed by application of the compounds to a bath solution in contact with and comprising cells having a channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

Preferably, the KCNQ2 that is a part of the potassium channel used in the assay will have the sequence provided in PCT/US98/13276 or a conservatively modified variant thereof. Alternatively, the KCNQ2 of the assay will be derived from a eukaryote.

KCNQ2 orthologs will generally confer substantially similar properties on a channel comprising such KCNQ2, as described above. In a preferred embodiment, the cell placed in contact with a compound that is suspected to be a KCNQ2 homolog is assayed for increasing or decreasing ion flux in a eukaryotic cell, e.g., an oocyte of Xenopus (e.g., *Xenopus laevis*) or a mammalian cell such as a CHO or HeLa cell. Channels that are affected by compounds in ways similar to KCNQ2 are considered homologs or orthologs of KCNQ2.

III. Pharmaceutical Compositions of Potassium Channel Openers

In another aspect, the present invention provides pharmaceutical compositions comprising a pharmaceutically acceptable excipient and a compound according to Formula II, above.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of formula (I) or a pharmaceutically acceptable salt of a compound of formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

IV. Methods for Increasing Ion Flow in Voltage-dependent Potassium Channels

In yet another aspect, the present invention provides methods for increasing ion flow through voltage dependent potassium channels in a cell, comprising contacting a cell containing the target ion channels with a compound of Formula II, above.

The methods provided in this aspect of the invention are useful for the diagnosis of conditions that can be treated by modulating ion flux through voltage-dependent potassium channels, or for determining if a patient will be responsive to therapeutic agents which act by opening potassium channels. In particular, a patient's cell sample can be obtained and contacted with a compound of Formula II and the ion flux can be measured relative to a cell's ion flux in the absence of a compound of Formula II. An increase in ion flux will typically indicate that the patient will be responsive to a therapeutic regimen of ion channel openers.

V. Methods for Treating Conditions Mediated by Voltage-dependent Potassium Channels In still another aspect, the present invention provides a method for the treatment of diseases or conditions mediated, at least in part, by voltage-dependent potassium channels. In this method, a subject suffering from such a condition or disease is administered an effective amount of a compound of Formula II.

The compounds provided herein are useful as potassium channel openers and find therapeutic utility via modulation of voltage-dependent potassium channels in the treatment of diseases or conditions. The potassium channels that are typically opened are described herein as voltage-dependent potassium channels such as the KCNQ potassium channels. As noted above, these channels may include homomultimers and heteromultimers of KCNQ2, KCNQ3, and KCNQ4. A heteromultimer of two proteins, e.g., KCNQ2 and KCNQ3 is referred to as, for example, KCNQ2/3. The conditions that can be treated with the compounds and compositions of the present invention may include, but are not limited to, central or peripheral nervous system disorders (e.g., migraine, ataxia, Parkinson's disease, bipolar disorders, spasticity, mood disorders, brain tumors, psychotic disorders, myokymia, seizures, epilepsy, hearing and vision loss, Alzheimer's disease, age-related memory loss, learning deficiencies, and motor neuron diseases, and as neuroprotective agents (e.g., to prevent stroke and the like)).

In therapeutic use for the treatment of epilepsy or other neurological conditions, the compounds utilized in the pharmaceutical method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

The materials, methods and devices of the present invention are further illustrated by the examples, which follow. These examples are offered to illustrate, but not to limit the claimed invention.

EXAMPLES

Example 1 sets forth representative methods of preparing 2-substituted -5-aminopyridines of use in preparing the compounds of the invention. The representative methods include the reduction of nitropyridines, rearrangement of nicotinic acids, and the displacement reactions of 2-halopyridines.

Examples 2 and 3 set forth a representative methods of preparing the benzanilides of the invention. Example 2 provides a method of preparing a benzanilide form an acid chloride. Example 3 provides a method of preparing a benzanilide from a carboxylic acid by generating the acid chloride in situ.

Example 4, 5, 6, and 7 set forth methods of elaborating the benzanilide nucleus. Example 4 provides a method of preparing 4-amino substituted benzanilides via a nucleophilic displacement. Example 5 provides a method for reducing an aromatic nitro group to the corresponding amine. Example 6 provides a method for preparing hydroxyl amine compounds. Example 7 provides a method for preparing sulfonamides.

Examples 8 and 9 set forth the characterization of a number of representative compounds of the invention. Example 8 sets forth the results of the physical characterization of the compounds. Example 9 sets forth the evaluation of the activity towards KCNQ2 of selected compounds of the invention.

General

In the examples below, unless otherwise stated, temperatures are given in degrees Celsius (°C.); operations were carried out at room or ambient temperature (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

General Experimental

Unless otherwise specified, all solvents (HPLC grade) and reagents were purchased from suppliers and used without further purification. Reactions were conducted under a blanket of argon unless otherwise stated. Analytical thin layer chromatography (tlc) was performed on Whatman Inc. 60 silica gel plates (0.25 mm thickness). Compounds were visualized under UV lamp (254 nM) or by developing with KMnO$_4$/KOH, ninhydrin or Hanessian's solution. Flash chromatography was done using silica gel from Selcetro Scientific (particle size 32–63). $^1$H NMR, $^{19}$F NMR and $^{13}$C NMR spectra were recorded on a Varian 300 machine at 300 MHz, 282 MHz and 75.7 MHz, respectively. Melting points were recorded on a Electrothermal IA9100 apparatus and were uncorrected.

EXAMPLE 1

Preparation of 2-substituted-5-aminopyridines 1.1 Reduction of Nitropyridines

Referring to Scheme 2, the desired aminopyridines (II) are prepared by reducing the corresponding nitropyridines (I). One skilled in the art will recognize that there are several methods to accomplish step 1. Tin chloride in DMF, hydrogenation using catalytic palladium and sodium borohydride in the presence of catalytic nickel chloride are known methods.

Scheme 2

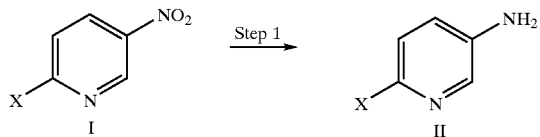

1.1a Synthesis of 5-amino-2-bromopyridine

Tin (II) chloride hydrate (0.78 g, 3.5 mmol) was added to a stirring solution of 5-nitro-2-bromopyridine (0.24 g, 1.2 mmol) in DMF (5 mL) at RT. After 2 h, 6N NaOH (2 mL) was added and the suspension was stirred vigorously for 10 min. The organics were extracted with diethyl ether (2×10 mL), washed with brine (2×10 mL) and dried (Na$_2$SO$_4$). The filtered solution was then concentrated under reduced pressure to afford the desired product as a yellow oil (0.178 g, 86%), which was used without further purification.

1.2 Rearrangement of Nicotinic Acids

Rearrangement of the corresponding nicotinic acids (III) (Scheme 3) using a modified Schmidt reaction, followed by deprotection of the aniline group generated the desired aminopyridines (IV) as the corresponding TFA salts.

Scheme 3

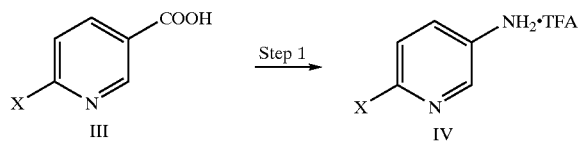

1.2 a Synthesis of 5-amino-2-methylpyridine (TFA salt)

A solution of diphenylphosphorylazide (430 μL, 2 mmol), triethylamine (278 μL, 2 mmol) and 6-methyl-nicotinic acid (274 mg, 2 mmol) in t-butanol (30 mL) was heated at reflux for 4 h. The solution was cooled to RT and poured into water (50 mL). The organics were extracted with ether (3×20 mL), washed with brine (2×10 mL) and dried (Na$_2$SO$_4$). Column chromatography (1:1 hexane/ethyl acetate) of the boc-protected aminopyridine gave the intermediate as a white solid (156 mg, 38%).

The desired 5-amino-2-methylpyridine-TFA salt was generated in situ by stirring in a 20% TFA/DCM solution (2 mL) for 4 h. The solution was concentrated under reduced pressure to afford a semi-solid, which was used without further purification.

1.2 b Synthesis of 5-amino-2-(trifluoromethyl)pyridine (TFA salt)

A solution of diphenylphosphorylazide (644 μL, 3 mmol), triethylamine (417 μL, 3 mmol) and 6-(trifluoromethyl)-nicotinic acid (573 mg, 3 mmol) in t-butanol (50 mL) was heated at reflux for 4 h, then cooled to RT and poured into water (50 mL). The organics were extracted with ether (3×20 mL), washed with brine (2×10 mL) and dried (Na$_2$SO$_4$). Column chromatography (1:1 hexane/ethyl acetate) of the boc-protected aniline gave the intermediate as a white solid (389 mg, 50%).

The desired 5-amino-2-methylpyridine-TFA salt was generated in situ by stirring in a 20% TFA/DCM solution (2 mL) for 4 h. The solution was concentrated under reduced pressure to afford a semi-solid, which was used without further purification.

1.3 Displacement of 2-halopyridines.

Several aminopyridines, which are not readily accessible via the methods outlined in schemes 1 or 2, may be synthesized via nucleophilic displacement of 2-chloropyridines as depicted in Scheme 4.

Scheme 4

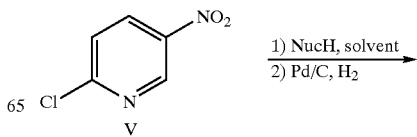

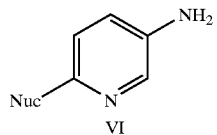

1.3 a Synthesis of 5-amino-2-fluoropyridine

A mixture of 5-nitro-2-chloropyridine (2.0 g, 12.6 mmol) and anhydrous potassium fluoride (2.2 g, 38 mmol) in a combination of sulfalone (6 mL) and benzene (4 mL) was stirred at RT for 20 min. The benzene was then removed by distillation. The resulting mixture was heated at 150° C. for 12 h. The mixture was cooled to RT whereupon water (60 mL) was added. The desired product was separated from the solution via steam distillation. Extraction of the distillate with diethyl ether (2×10 mL) followed by drying ($Na_2SO_4$) and concentration gave 5-nitro-2-fluoropyridine as a water white oil (1.3 g, 73%).

10% Palladium on charcoal (20 mg, cat) was added to a stirring solution of 5-nitro-2-fluoropyridine (100 mg, 0.7 mmol) in dichloromethane (3 mL) at RT. 1 atmosphere of hydrogen gas was then applied to the solution and the mixture was stirred at RT for 1 h. The mixture was passed through a short plug of celite and the resulting solution, containing the desired 5-amino-2-fluoropyridine, was used without further purification.

EXAMPLE 2
Preparation of Benzanilides from Acid Chlorides

Benzanilides (e.g., VIII) were prepared by reacting acid chlorides (e.g., VII) with aminopyridines (e.g., II, IV and VI) as shown in Scheme 5. The reaction was typically conducted in the presence of a tertiary amine base such as triethylamine in an organic solvent such as dichloromethane or tetrahydrofuran, and at room temperature.

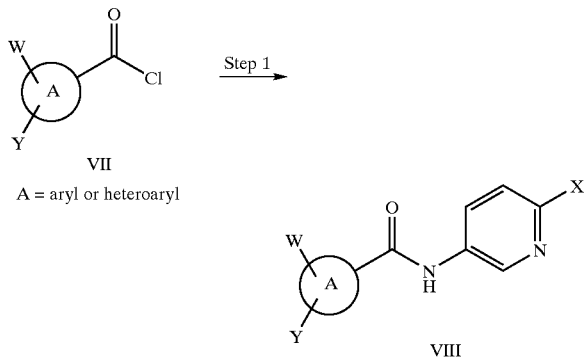

2.1 General Experimental for Scheme 5

A solution of acid chloride (VII) (1 mmol) in a dry solvent (e.g., acetonitrile, THF, DCM) (3 mL) was added dropwise to a stirring solution of aminopyridine (II or VI) (1 mmol) and N, N-diisopropylethylamine (1.2 mmol) in a dry solvent (e.g., acetonitrile, THF, DCM) (5 mL) at RT. The resulting solution was stirred for an additional 1 h. If TLC analysis indicated presence of starting aniline the solution was heated at 55° C. for another 1 h. After cooling to room temperature ethyl acetate (10 mL) was added and the solution was washed with water (2×10 mL) and dried ($Na_2SO_4$). The solvent was removed under reduced pressure and the crude material was purified by column chromatography (hexanes/ethyl acetate) or by crystallization (hexane/dichloromethane). The products were typically white solids (50–98%). Compounds prepared via this procedure include, 1–15, 25, 27, 29 and 42.

2.1a Preparation of N-[2-chloro-5-pyridyl]-3-(trifluoromethyl)benzamide (3)

To a stirring solution of 5-amino-2-chloropyridine (129 mg, 1 mmol) and N,N-diisopropylethylamine (209 µL, 1.2 mmol) in dry acetonitrile (5 mL) was added 3-(trifluoromethyl)benzoyl chloride (151 µL, 1 mmol). The resulting solution was heated at 55° C. for 3 h. After cooling to room temperature ethyl acetate (10 mL) was added and the solution was washed with water (2×10 mL) and dried ($Na_2SO_4$). The solvent was removed under reduced pressure and the crude material was purified by column chromatography (4:1, hexane/ethyl acetate) to afford the desired product as a white solid (284 mg, 94%).

EXAMPLE 3
Preparation of Benzanilides from Acids

Benzanilides (VIII) may be also be prepared from acids (IX) by initially converting them to their acid chlorides (VII). Acids (IX) were treated with oxalyl chloride in the presence of catalytic N, N-dimethylformamide in an organic solvent such as dichloromethane or tetrahydrofuran preferably at 0° C. The acid chloride, generated in situ was then reacted with aminopyridines (II, IV or VI) in the presence of a tertiary amine base such as triethylamine in an organic solvent such as dichloromethane or tetrahydrofuran. The reactions were typically performed at RT.

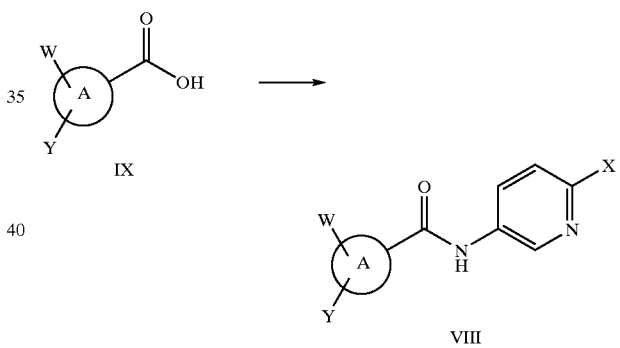

3.1 General Experimental for Scheme 6

Oxalyl chloride (1.05 mmol) was added dropwise to a stirring suspension of acid (IX) (1 mmol) and DMF (0.1 mmol) in dry DCM (5 mL) at 0° C. Once addition was complete the reaction was allowed to warm to RT and stirred for a further 45 min whereupon the reaction was a clear solution. This solution was added dropwise to a stirring solution of aminopyridine (II or VI) (0.95 mmol) and N, N-diisopropylethylamine (2.2 mmol) in DCM (5 mL) at RT. After 30 min the organics were washed with aqueous 1N NaOH (10 mL), brine (10 mL) and dried ($Na_2SO_4$). The filtered solution was concentrated under reduced pressure and the crude product was purified by column chromatography (hexanes/ethyl acetate) or by crystallization (hexane/dichloromethane). Compounds prepared via this procedure include, compounds 16–24, 26, 28 and 37.

EXAMPLE 4
Preparation of 4-Amino Substituted Benzamides via Nucleophilic Displacement Aryl fluorides (X) (Scheme 7) possessing strongly electron withdrawing groups in either the ortho or para positions were displaced with primary or secondary amines under elevated temperatures in a polar organic solvent such as DMSO or NMP to yield compounds of the formula (XI).

Scheme 7

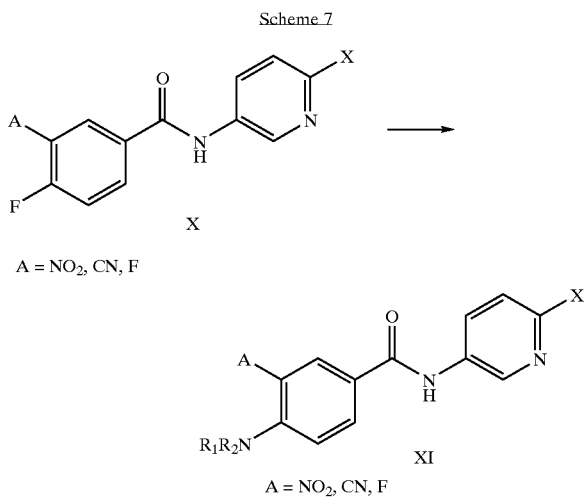

A = NO₂, CN, F

4.1 General Experimental for Scheme 7

A solution of amine (1.1 mmol) and (X) (1 mmol) in either dry NMP or DMSO (3 mL) was heated at 120° C. for 12 h. After cooling to RT, water (10 mL) and ethyl acetate (10 mL) were added. After vortexing for several minutes the organic layer was removed and dried (Na₂SO₄). The solvent was removed under reduced pressure and the residue purified by column chromatography (hexanes/ethyl acetate or acetone/chloroform). The products (XI) were obtained as white solids (30–50%). Compounds prepared via this procedure include, compounds 30–34.

EXAMPLE 5
Reduction of Aromatic Nitro to Amine

Scheme 8 outlines a general synthetic route to compounds of formulae (XIII) and (XIV).

Scheme 8

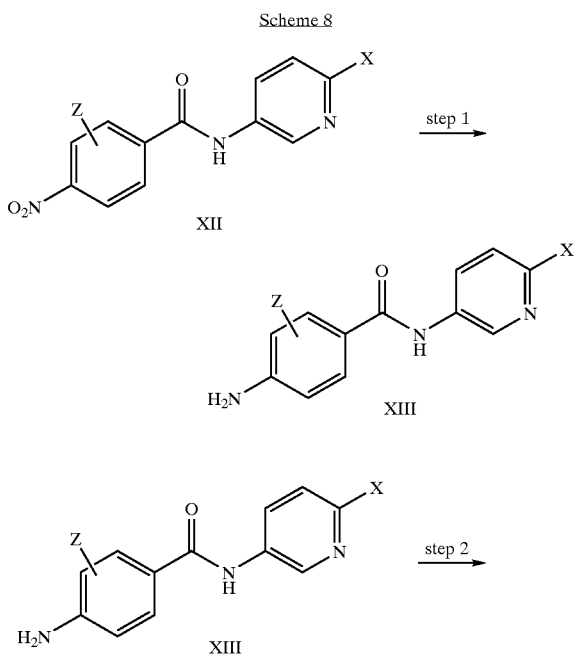

-continued

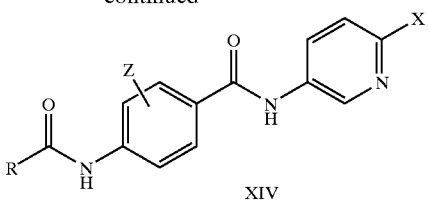

5.1 General Experimental for Scheme 8

Compounds of structure (XII) were prepared using either general procedure B or C. Tin (II) chloride hydrate (22 mmol) was added to a stirring solution of (XII) in DMF (20 mL) at RT. After 14 h, 6N NaOH (6 mL) was added and the suspension was stirred vigorously for 10 min. The organics were extracted with ethyl acetate (2×20 mL), washed with brine (2×10 mL) and dried (Na₂SO₄). The filtered solutions were concentrated under reduced pressure and the crude products were purified by column chromatography (hexanes/ethyl acetate; 1:2) to afford the desired intermediates (XIII) as a white solids (60–90%).

The intermediates (XIII) (0.2 mmol) were coupled with either acid chlorides (VI) or acids (0.2 mmol) using the methods described in general procedures A and B. The desired products (XIV) were obtained as tan solids (20–60%). Compounds prepared via this procedure include, compound 35.

EXAMPLE 6
Preparation of 4-Hydroxyamino Compounds (XV).

Hydroxyamines (XV) were prepared according to the synthetic route outlined in Scheme 9.

Scheme 9

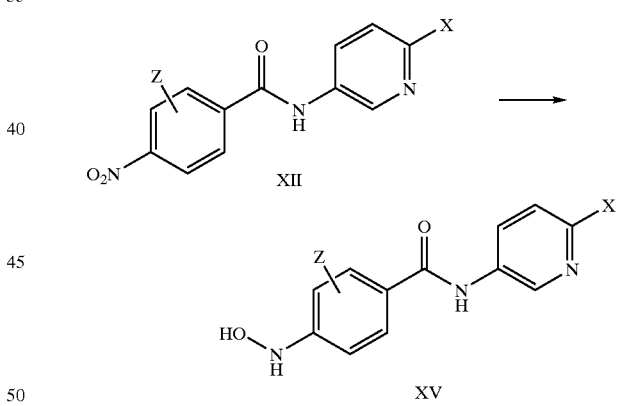

6.1 General Experimental for Scheme 9

Tin (II) chloride hydrate (3 mmol) was added to a stirring solution of nitrobenzamide (XII) (1 mmol) in DMF (5 mL) at RT. After 3 h, 6N NaOH (6 mL) was added and the suspension was stirred vigorously for 10 min. The organics were extracted with ethyl acetate (2×20 mL), washed with brine (2×10 mL) and dried (Na₂SO₄). The filtered solution was then concentrated under reduced pressure to afford the crude product. Purification by column chromatography (ethyl acetate) gave the desired products (XV) as beige solids (50–70%).

EXAMPLE 7
Preparation of Sulfonamides

Sulfonamides (e.g., XVIII) were prepared using the chemistry outlined in Scheme 10. Intermediate (XVII) were generated by coupling an aminopyridine (II or IV) with an activated form of (XVI). Subsequent coupling of the sulfonyl group with an amine generated the desired sulfonamides (XVIII)

Scheme 10

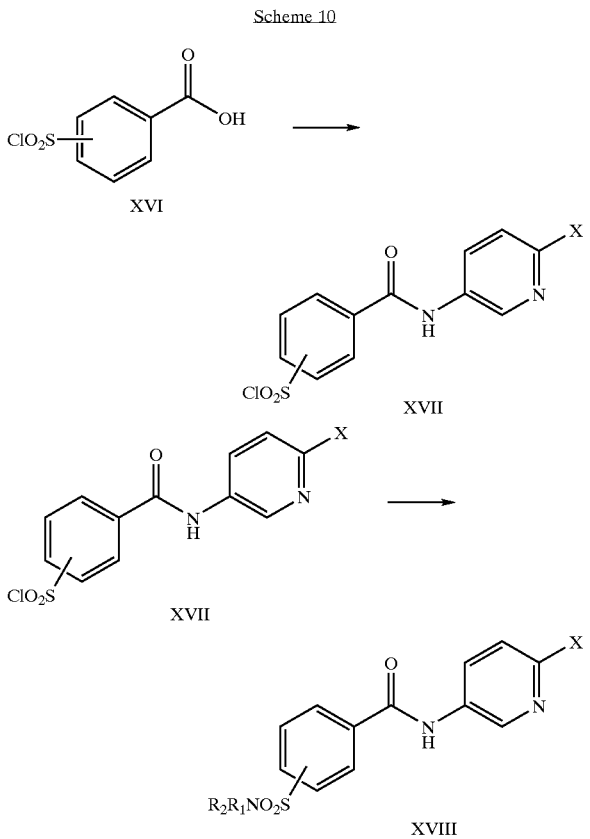

7.1 General Experimental for Scheme 10

Oxalyl chloride (175 μL, 2 mmol) was added dropwise to a stirring solution of (XVI) (440 mg, 2 mmol) and DMF (20 μL, cat) in THF (8 mL) at 0° C. After addition was complete the reaction was allowed to warm to RT. After 30 min the reaction was cooled back to 0° C. whereupon a solution of (II or IV) (1.9 mmol) and N, N-diisopropylethylamine (700 μL, 4 mmol) in THF (2.3 mL) was added. After stirring for 30 min at RT, this solution of (XVII) (0.18 M) was used directly without further manipulation.

A solution of (XVII) (5.5 mL, 1 mmol) in THF was added to a stirring solution of amine (1 mmol) and N, N-diisopropylethylamine (3 mmol) in THF (2 mL) at RT. After 1 h, water (10 mL) and ethyl acetate (10 mL) were added. The organic layer was separated, washed with water (5 mL), aqueous 1N NaOH (5 mL), aqueous 1N HCl (5 mL) and then dried (Na$_2$SO$_4$). The solvent was removed under reduced pressure and the residue purified by column chromatography (hexanes/ethyl acetate; 1:2). The products were obtained as white solids (60–80%). Compounds prepared via this procedure include, compounds 36 and 40.

EXAMPLE 8

The compounds of the invention were characterized using a combination of melting point, $^1$H NMR and mass spectrometry. The results of the characterization are presented below. The structures for the compounds set forth below are provided in FIG. 1.

3,4-Dichloro-N-pyridin-3-yl-benzamide (1): mp 165–166° C.; $^1$H NMR (300 MHz, DMSO-d$_6$) δ10.58 (1H, brs), 8.87 (1H, d, J=2.3 Hz), 8.30 (1H, dd, J=4.7, 1.4 Hz), 8.19 (1H, d, J=1.9 Hz), 8.16–8.12 (1H, m), 7.91 (1H, dd, J=8.4, 2.1 Hz), 7.80 (1H, d, J=8.5 Hz) and 7.38 (1H, dd, J=8.4, 4.7 Hz); MS (ESI) m/z: 266.9 [M+H]$^+$.

3,4-Dichloro-N-(6-chloro-pyridin-3-yl)-benzamide (2): mp 188–189° C.;$^1$H NMR (300 MHz, CDCl$_3$) δ7.36 (1H,d, J=8.7 Hz), 7.58 (1H, d, J=9.3 Hz), 7.70 (1H, dd, J=8,4, 2.0 Hz), 7.90 (1H, brs), 7.96 (1H, d, J=1.9 Hz), 8.24 (1H, dd, J=8.7, 2.8 Hz) and 8.48 (1H, d, J=2.8 Hz); $^{13}$C NMR (75 MHz, DMSO-d$_6$) δ124.7, 128.6, 130.2, 131.4, 131.9, 134.8, 135.4, 142.0, 144.9 and 164.0; MS (ESI) m/z: 301.1 [M+H]$^+$.

N-(6-Chloro-pyridin-3-yl)-3-trifluoromethyl-benzamide (3): mp 139–140° C.; $^1$H NMR (300 MHz, CDCl$_3$) δ7.35 (1H, d, J=8.7 Hz), 7.63 (1H, t, J=7.8 Hz), 7.82 (1H, d, J=7.8 Hz), 8.06 (1H, d, J=7.8 Hz), 8.11 (1H, brs), 8.25 (1H, dd, J=8.7, 2.9 Hz), 8.36 (1H, s) and 8.50 (1H, d, J=2.6 Hz); $^{19}$F NMR (282 MHz, CDCl$_3$) δ−63.6; $^{13}$C NMR (75 MHz, DMSO-d$_6$) δ124.2, 124.2, 124.6, 129.0, 129.7, 130.6, 130.9, 133.7, 134.6, 141.2 and 164.8; MS (ESI) m/z: 301.2 [M+H]$^+$.

N-(6-Chloro-pyridin-3-yl)-3,4-difluoro-benzamide (4): mp; 164° C.; $^1$H NMR (300 MHz, DMSO-d$_6$) δ7.51 (1H, d, J=8.7 Hz), 7.59–7.68 (1H, m), 7.84–7.88 (1H, m), 8.03 (1H, ddd, J=11.3, 7.9, 2.1 Hz), 8.19–8.23 (1H, m), 8.25 (1H, d, J=2.0 Hz) and 10.64 (1H, s); $^{19}$F NMR (282 MHz, DMSO-d$_6$) δ−112.9 (m), −115.2 (m); $^{13}$C NMR (75 MHz, DMSO-d$_6$) δ117.9 (dd, J=18.3, 49.8 Hz), 124.7, 125.7 (dd, J=3.4, 6.9 Hz), 131.5 (m), 131.9, 135.3, 142.1, 145.0, 149.3 (dd, J=14.7, 201.0 Hz), 152.8 (dd, J=12.6, 205.0 Hz), 164.6; MS (ESI) m/z: 269.1 [M+H]$^+$.

3-Chloro-N-(6-chloro-pyridin-3-yl)-benzamide (5): mp 153–154° C.; $^1$H NMR (300 MHz, DMSO-d$_6$) δ10.67 (1H, brs), 8.74 (1H, d, J=2.6 Hz), 8.22 (1H, dd, J=8.7, 2.8 Hz), 7.99 (1H, d, J=1.7 Hz), 7.90 (1H, d, J=7.8 Hz), 7.69 (1H, d, J=7.1 Hz), 7.58 (1H, t, J=7.8 Hz) and 7.51 (1H, d, J=8.7 Hz); MS (ESI) m/z: 267.0 [M+H]$^+$.

Biphenyl-4-carboxylic acid (6-chloro-pyridin-3-yl)-amide (6): mp 227–229° C.; $^1$H NMR (300 MHz, DMSO-d$_6$) δ10.62 (1H, brs), 8.81 (1H, d, J=2.3 Hz), 8.26 (1H, dd, J=8.7 2.4 Hz), 8.06 (2H, d, J=8.2 Hz), 7.85 (2H, d, J=8.2 Hz), 7.75 (2H, d, J=7.5 Hz), 7.53–7.47 (3H, m) and 7.42 (1H, q, J=7.1 Hz); MS (ESI) m/z: 309.2 [M+H]$^+$.

6-Chloro-N-(6-chloro-pyridin-3-yl)-nicotinamide (7): mp 228° C.; $^1$H NMR (300 MHz, DMSO-d6) δ10.81 (1H, brs), 8.92 (1H, d, J=2.3 Hz), 8.73 (1H, d, J=2.6 Hz), 8.32 (1H, dd, J=8.4, 2.4 Hz), 8.19 (1H, dd, J=8.7, 2.8 Hz), 7.71 (1H, d, J=8.4 Hz) and 7.52 (1H, d, J=8.7 Hz); MS (ESI) m/z: 268.1 [M+H]$^+$.

3,4-Difluoro-N-(6-methyl-pyridin-3-yl)-benzamide (8): $^1$H NMR (300 MHz, DMSO-d$_6$) δ10.42 (1H, brs), 8.73 (1H, d, J=2.3 Hz), 8.04–7.97 (2H, m), 7.86–7.82 (1H, m), 7.90 (1H, dt, J=10.4, 8.4 Hz), 7.23 (1H, d, J=8.5 Hz) and 2.42 (3H, s); $^{19}$F NMR (282 MHz, DMSO-d$_6$) δ−133.1 to −133.3 (1H, m) and −137.1 (1H, q, J=10.7 Hz); MS (ESI) m/z: 249.0 [M+H]$^+$.

N-(6-Chloro-pyridin-3-yl)-3-fluoro-benzamide (9): mp 160° C.; $^1$H NMR (300 MHz, DMSO-d$_6$) δ10.63 (1H, brs), 8.75 (1H, d, J=2.8 Hz), 8.20 (1H, dd, J=8.7, 2.8 Hz), 7.79 (1H, d, J=7.8 Hz), 7.75 (1H, d, J=11.1 Hz), 7.62–7.55 (1H, m) and 7.53–7.43 (2H, m); $^{19}$F NMR (282 MHz, DMSO-d$_6$) δ−112.0 (q, 8.5Hz); MS (ESI) m/z: 251.0 [M+H]$^+$.

N-(6-Chloro-pyridin-3-yl)-3-(trifluoromethyl)-benzamide (10): mp 169–170° C.; $^1$H NMR (300 MHz, DMSO-d$_6$) δ10.81 (1H, brs), 8.75 (1H, d, J=2.8 Hz), 8.22 (1H, dd, J=8.7, 2.8 Hz), 8.13 (1H, d, J=8.2 Hz), 7.91 (2H, d, J=8.4 Hz) and 7.52 (2H, d, J=8.7 Hz); ¹⁹F NMR (282 MHz, DMSO-d₆) δ−61.4 (s); MS (ESI) m/z: 301.2 [M+H]⁺.

N-(6-Chloro-pyridin-3-yl)-4-fluoro-3-trifluoromethyl-benzamide (11): mp 149–150° C.; ¹H NMR (300 MHz, DMSO-d₆) δ10.63 (1H, brs), 8.76 (1H, d, J=2.6 Hz), 8.22 (1H, dd, J=8.7, 2.8 Hz), 7.98 (2H, d, J=8.7 Hz), 7.63 (1H, d, J=8.7 Hz) and 7.52 (1H, d, J=8.7 Hz); MS (ESI) m/z: 319.1 [M+H]⁺.

N-(6-Chloro-pyridin-3-yl)-3-fluoro-4-trifluoromethyl-benzamide (12): mp 182° C.; ¹H NMR (300 MHz, DMSO-d6) δ10.78 (1H, brs), 8.75 (1H, d, J=2.3 Hz), 8.37–8.32 (2H, m), 8.22 (1H, dd, J=8.7, 2.6 Hz), 7.73 (1H, m) and 7.54 (1H, d, J=8.7 Hz); ¹⁹F NMR (282 MHz, DMSO-d₆) δ−60.1 (3F, m), −110.7 (m); MS (ESI) m/z: 319.1 [M+H]⁺.

N-(6-Chloro-pyridin-3-yl)-4-fluoro-benzamide (13): mp 163–164° C.; ¹H NMR (300 MHz, DMSO-d₆) δ10.58 (1H, brs), 8.76 (1H, d, J=2.6 Hz), 8.22 (1H, dd, J=8.7, 2.6 Hz), 8.04 (1H, d,J=8.7 Hz), 8.02 (1H, d,J=8.7 Hz), 7.51 (1H, d, J=8.7 Hz) and 7.39 (2H, t, J=8.8 Hz); ¹⁹F NMR (282 MHz, DMSO-d₆) δ−107.7 (m); MS (ESI) m/z: 319.0 [M+H]⁺.

N-(6-Chloro-pyridin-3-yl)-4-chloro-benzamide (14): mp 197–199° C.; ¹H NMR (300 MHz, DMSO-d₆) δ10.63 (1H, brs), 8.76 (1H, d, J=2.6 Hz), 8.22 (1H, dd, J=8.7, 2.8 Hz), 7.98 (2H, d, J=8.7 Hz), 7.63 (1H, d, J=8.7 Hz) and 7.52 (1H, d, J=8.7 Hz); MS (ESI) m/z: 267.0 [M+H]⁺.

5,6-Difluoro-N-(6-fluoro-pyridin-3-yl)-nicotinamide (15): mp 135–137° C.; ¹H NMR (300 MHz, DMSO-d₆) δ10.58 (1H, brs), 8.52 (1H, s), 8.29–8.23 (1H, m), 8.03–7.97 (1H, m), 7.87–7.82 (1H, m), 7.65–7.56 (1H, m) and 7.19 (1H,dd, J=8.9, 3.1 Hz); ¹⁹F NMR (282 MHz, DMSO-d₆) δ−73.6 (1F, d, J=6.5 Hz), −132.9 (1H, q, J=10.7Hz) and −137.1 (1H, q, J=10.7 Hz); MS (ESI) m/z: 253.0 [M+H]⁺.

N-(6-Chloro-pyridin-3-yl)-3-methyl-4-nitro-benzamide (16): mp 192–193° C.; ¹H NMR (300 MHz, DMSO-d₆) δ10.81 (1H, brs), 8.74 (1H, d, J=2.6 Hz), 8.21 (1H, dd, J=8.7, 2.8 Hz), 8.09 (1H, d, J=8.4 Hz), 8.02 (1H, s), 7.94 (1H, dd, J=8.5, 1.6 Hz), 7.52 (1H, d, J=8.7 Hz) and 2.58 (3H, s); MS (ESI) m/z: 292.2 [M+H]⁺.

5-Fluoro-1H-indole-2-carboxylic acid (6-chloro-pyridin-3-yl)-amide (17): mp 290° C.; ¹H NMR (300 MHz, DMSO-d₆) δ11.92 (1H, brs), 10.58 (1H,brs), 8.79 (1H, s), 8.25 (1H, dd, J=8.7 and 2.4 Hz), 7.53–7.41 (4H, m) and 7.10 (1H, t, J=7.1 Hz); ¹⁹F NMR (282 MHz, DMSO-d₆) δ−123.0 (m); MS (ESI) m/z: 290.0 [M+H]⁺.

5-Chloro-1H-indole-2-carboxylic acid (6-chloro-pyridin-3-yl)-amide (18): mp 296° C.; ¹H NMR (300 MHz, DMSO-d₆) δ12.03 (1H, brs), 10.62 (1H, brs), 8.80 (1H, d, J=2.6 Hz), 8.24 (1H, dd, J=8.7 and 2.6 Hz), 7.79 (1H, s) 7.52 (1H, d, J=8.7 Hz), 7.42 (1H, d, J=8.9 Hz), 7.41 (1H, s) and 7.23 (1H, dd, J=8.7, 1.9 Hz); MS (ESI) m/z: 306.0 [M+H]⁺.

5-Chloro-benzofuran-2-carboxylic acid (6-chloro-pyridin-3-yl)-amide (19): mp 222–223° C.; ¹H NMR (300 MHz, DMSO-d6) δ11.00 (1H, brs), 8.78 (1H, d, J=2.6 Hz), 8.24 (1H, dd, J=8.7, 2.8 Hz), 7.90 (1H, d, J=2.1 Hz), 7.76 (1H, s,), 7.73 (1H, d, J=8.9 Hz) and 7.51 (2H, d, J=8.9 Hz); MS (ESI) m/z: 306.9 [M+H]⁺.

5-Chloro-thiophene-2-carboxylic acid (6-chloro-pyridin-3-yl)-amide (20): mp 215–216° C.; ¹H NMR (300 MHz, DMSO-d₆) δ10.61 (1H, brs), 8.68 (1H, d, J=2.8 Hz), 8.14 (1H, dd, J=8.7, 2.6 Hz), 7.88 (1H, d, J=4.2 Hz), 7.50 (1H, d, J=8.5 Hz) and 7.27 (1H, d, J=4.0 Hz); ¹³C NMR (75 MHz, DMSO-d₆) δ159.7, 144.8, 142.0, 138.5, 135.3, 135.2, 131.5, 130.4, 129.0 and 124.7.0; MS (ESI) m/z: 273.0 [M+H]⁺.

5-Chloro-furan-2-carboxylic acid (6-chloro-pyridin-3-yl)-amide (21): mp 143–144° C.; ¹H NMR (300 MHz, DMSO-d₆) δ10.59 (1H, brs), 8.72 (1H, d, J=2.4 Hz), 8.18 (1H, dd, J=8.7, 2.6 Hz), 7.50 (1H, d, J=8.7 Hz), 7.43 (1H, d,J=3.5 Hz) and 6.76 (1H, d, J=3.7 Hz); MS (ESI) m/z: 257.1 [M+H]⁺.

4,5-Dichloro-isothiazole-3-carboxylic acid (6-chloro-pyridin-3-yl)-amide (22): mp 199–201° C.; ¹H NMR (300 MHz, DMSO-d₆) δ11.16 (1H, brs), 8.75 (1H, d, J=2.6 Hz), 8.20 (1H, dd, J=8.7, 2.8 Hz) and 7.51 (1H, d, J=8.7 Hz); MS (ESI) m/z: 307.9[M+H]⁺.

3-Methyl-1H-indole-2-carboxylic acid (6-chloro-pyridin-3-yl)-amide (23): mp 184–185° C.; ¹H NMR (300 MHz, DMSO-d₆) δ10.64 (1H, brs), 8.75 (1H, d, J=2.6 Hz), 8.21 (1H, dd, J=8.7,2.8 Hz), 7.68 (1H, d, J=8.0 Hz), 7.54 (1H, d, J=8.5 Hz), 7.50 (2H, d, J=8.9 Hz), 7.34 (1H, s), 7.31 (1H, t, J=7.1 Hz), 7.13 (1H, t, J=7.1 Hz) and 3.98 (3H, s); MS (ESI) m/z: 286.1 [M+H]⁺.

5-Ethyl-1H-indole-2-carboxylic acid (6-chloro-pyridin-3-yl)-amide (24): mp 270° C.; ¹H NMR (300 MHz, DMSO-d₆) δ11.67 (1H, brs), 10.49 (1H, brs), 8.80 (1H, s), 8.25 (1H, dd, J=8.7 and 2.8 Hz), 7.51 (1H, d, J=8.7 Hz), 7.46 (1H, s), 7.36 (1H, d, J=8.7 Hz), 7.35 (1H, s), 7.10 (1H, d, J=8.5 Hz), 2.66 (2H, q, J=7.7 Hz) and 1.21 (1H, t, J=7.7 Hz); ¹³C NMR (75 MHz, DMSO-d₆) δ160.6, 144.3, 141.7, 136.2, 136.0, 131.1, 127.6, 125.6, 124.7, 120.4, 112.8, 104.8, 28.8 and 16.8; MS (ESI) m/z: 300.2 [M+H]⁺.

N-(6-Chloro-pyridin-3-yl)-benzamide (25): mp 163–164° C.; ¹H NMR (300 MHz, DMSO-d₆) δ10.59 (1H, brs), 8.74 (1H, d, J=2.6 Hz), 8.21 (1H, dd, J=8.7, 2.8 Hz), 7.94 (1H, s), 7.92 (1H, d, J=1.6 Hz), 7.59 (1H, d, J=7.1 Hz) and 7.55–7.49 (3H, m); MS (ESI) m/z: 233.0 [M+H]⁺.

1H-Indole-2-carboxylic acid (6-chloro-pyridin-3-yl)-amide (26): mp 260–263° C.; ¹H NMR (300 MHz, DMSO-d₆) δ11.85 (1H, brs), 10.62 (1H, brs), 8.78 (1H, d, J=2.6 Hz), 8.23 (1H, dd, J=8.7, 2.8 Hz), 7.66 (1H, d, J=8.0 Hz), 7.51 (1H, d, J=8.5 Hz), 7.45 (1H, d, J=8.4 Hz), 7.41–7.40 (1H, m), 7.23 (1H, t, J=7.1 Hz) and 7.06 (1H, d, J=7.3 Hz); MS (ESI) m/z: 272.0 [M+H]⁺.

Benzo[b]thiophene-2-carboxylic acid (6-chloro-pyridin-3-yl)-amide (27): mp 226–227° C.; ¹H NMR (300 MHz, DMSO-d₆) δ10.86 (1H, brs), 8.75 (1H, d, J=2.6 Hz), 8.34 (1H, s), 8.21 (1H, dd, J=8.7, 2.8 Hz), 8.06–7.99 (2H, m) and 7.54–7.48 (3H, m); MS (ESI) m/z: 289.1 [M+H]⁺.

5-Fluoro-1H-indole-2-carboxylic acid (6-methyl-pyridin-3-yl)-amide (28): mp 303–304° C.; ¹H NMR (300 MHz, DMSO-d₆) δ11.88 (1H, brs), 10.36 (1H, brs), 9.05 (1H, d, J=1.9 Hz), 8.06 (1H, dt, J=8.4, 2.1 Hz), 7.45 (2H, m), 7.39 (1H, s), 7.24 (1H, d, J=8.3 Hz), 7.08 (1H, dt, J=9.2, 2.4 Hz) and 2.43 (3H, s); ¹⁹F NMR (282 MHz, DMSO-d₆) δ−123.2; MS (ESI) m/z: 270.2 [M+H]⁺.

3,4-Difluoro-N-(6-trifluoromethyl-pyridin-3-yl)-benzamide (29): mp 175–176° C.; ¹H NMR (300 MHz, DMSO-d₆) δ10.84 (1H, brs), 9.05 (1H, d, J=1.8 Hz), 8.45 (1H, dd, J=8.5, 1.9 Hz), 8.07 (1H, ddd, J=9.9, 7.6, 2.1 Hz), 7.93 (1H, d, J=8.5 Hz) and 7.89–7.86 (1H, m); ¹⁹F NMR (282 MHz, DMSO-d₆) δ−65.7 (3F, s), −132.5 (1F, m) and −137.0 (1F, m); MS (ESI) m/z: 303.1 [M+H]⁺.

N-(6-Chloro-pyridin-3-yl)-3-fluoro-4-pyrrolidin-1-yl-benzamide (30): mp 215–216° C.; ¹H NMR (300 MHz, DMSO-d₆) δ10.23 (1H, brs), 8.71 (1H, d, J=2.6 Hz), 8.18 (1H, dd, J=8.7, 2.4 Hz), 7.70 (1H, s), 7.65 (1H, d, J=3.1 Hz), 7.46 (1H, d, J=8.9 Hz), 6.73 (1H, t, J=8.5 Hz), 3.42–3.40 (4H, m) and 1.91–1.88 (4H, m); ¹⁹F NMR (282 MHz, DMSO-d₆) δ−129.0 (s); MS (ESI) m/z: 320.2 [M+H]⁺.

N-(6-Chloro-pyridin-3-yl)-3-fluoro-4-morpholin-4-yl-benzamide (31): mp 228–229° C.; ¹H NMR (300 MHz, DMSO-d$_6$) δ10.41 (1H, s), 8.75 (1H, d, J=2.6 Hz), 8.20 (1H, dd, J=8.7 and 2.6 Hz), 7.79 (1H, s), 7.74 (1H, d, J=7.7 Hz), 7.50 (1H, d, J=8.7 Hz), 7.13 (1H, t, J=9.2 Hz), 3.74 (4H, m) and 3.12 (4H, m); $^{13}$C NMR (75 MHz, DMSO-d$_6$) δ164.8, 155.7, 152.5, 144.4, 143.3 (d, J=7 Hz), 142.0, 135.9, 131.4, 127.3 (d, J=7 Hz), 125.5, 124.6, 118.7 (d, J=3 Hz), 66.5 and 50.4 (d, J=5 Hz); MS (ESI) m/z: 336.2 [M+H]$^+$.

N-(6-Chloro-pyridin-3-yl)-3-fluoro-4-imidazol-1-yl-benzamide (32): mp 215–218° C.; $^1$H NMR (300 MHz, DMSO-d$_6$) δ10.71 (1H ,s), 8.78 (1H, s), 8.24 (1H, dt, J=8.7, 1.6 Hz), 8.17 (1H, s), 8.07 (1H, dd, J=12.0, 1.6 Hz), 7.96 (1H, dd, J=8.4, 1.7 Hz), 7.88 (1H, t, J=8.2 Hz), 7.69 (1H, s), 7.53 (1H, d, J=8.7 Hz) and 7.17 (1H, s); $^{19}$F NMR (282 MHz, DMSO-d$_6$) δ–123.1 (t, J=8.8 Hz); MS (ESI) m/z: 317.1 [M+H]$^+$.

N-(6-Chloro-pyridin-3-yl)-3-fluoro-4-[(pyridin-2ylmethyl)-amino]-benzamide (33): mp 210–211° C.; $^1$H NMR (300 MHz, DMSO-d$_6$) δ10.20 (1H, brs), 8.69 (1H, d, J=2.6 Hz), 8.50 (1H, d, J=4.7 Hz), 8.15 (1H, dd, J=8.7, 2.8 Hz), 7.75–7.64 (2H, m), 7.45 (1H, d, J=8.7 Hz), 7.31 (1H, d, J=8.0 Hz), 7.25 (1H, dd, J=6.4, 5.1 Hz), 6.63 (1H, t, J=8.7 Hz) and 4.49 (2H, d, J=5.9 Hz); $^{19}$F NMR (282 MHz, DMSO-d$_6$) δ–134.3 (m); MS (ESI) m/z: 357.0 [M+H]$^+$.

N-(6-Chloro-pyridin-3-yl)-4-dimethylamino-3-fluoro-benzamide (34): mp 170–171° C.; $^1$H NMR (300 MHz, DMSO-d$_6$) δ10.32 (1H, brs), 8.76 (1H, s), 8.21 (1H, d, J=8.7 Hz), 7.75 (1H, s), 7.71 (1H, d, J=5.8 Hz), 7.59 (1H, d, J=8.7 Hz), 7.02 (1H, t, J=9.2 Hz) and 2.92 (6H, s); $^{19}$F NMR (282 MHz, DMSO-d$_6$) δ–122.6 (t, J=10.7 Hz); MS (ESI) m/z: 294.2 [M+H]$^+$.

Pyridine-2-carboxylic acid [4-(6-chloro-pyridin-3-ylcarbamoyl)-phenyl]-amide (35): mp 258–260° C.; $^1$H NMR (300 MHz, DMSO-d$_6$) δ10.92 (1H, s), 10.50 (1H, s), 8.78 (1H, d, J=2.6 Hz),), 8.75 (1H, d, J=4.7 Hz), 8.24 (1H, dd, J=8.7 and 2.6 Hz), 8.17 (1H, d, J=7.8 Hz), 8.09 (2H, d, J=7.8 Hz), 8.08 (1H, m), 7.98 (2H, d, J=8.7 Hz), 7.70 (1H, dd, J=6.4, 5.0 Hz) and 7.50 (1H, d, J=8.7 Hz); $^{13}$C NMR (75 MHz, DMSO-d$_6$) δ165.8, 163.5, 150.0, 149.0, 144.4, 142.3, 141.9, 138.8, 136.1, 131.4, 129.4, 129.2, 127.7, 124.6, 123.1 and 120.1; MS (ESI) m/z: 353.2 [M+H]$^+$.

N-(6-Chloro-pyridin-3-yl)-4-(morpholine-4-sulfonyl)-benzamide (36): $^1$H NMR (300 MHz, DMSO-d$_6$) δ10.88 (1H, s), 8.78 (1H, d, J=2.6 Hz), 8.24 (1H, dd, J=8.7 and 2.6 Hz), 8.19 (2H, d, J=8.5 Hz), 7.90 (2H, d, J=8.5 Hz), 7.50 (1H, d, J=8.7 Hz), 3.62 (4H, m) and 2.90 (4H, m); $^{13}$C NMR (75 MHz, DMSO-d$_6$) δ165.3, 144.9, 142.1, 138.8, 137.9, 135.7, 131.5, 129.4, 128.3, 124.7, 65.8 and 46.8; MS (ESI) m/z: 382.1 [M+H]$^+$.

N-(6-Chloro-pyridin-3-yl)-3-fluoro-4-nitro-benzamide (37): mp 205° C.; $^1$H NMR (300 MHz, DMSO-d$_6$) δ10.87 (1H, brs), 8.69 (1H, d, J=2.4 Hz), 8.32 (1H, t, J=7.8 Hz), 8.22 (1H, dd, J=8.7, 2.6 Hz), 8.10(1H, dd, J=11.8, 1.6 Hz), 7.96 (1H, d, J=8.5 Hz) and 7.53 (1H, d, J=8.7 Hz); MS (ESI) m/z: 294.0 [M–H]$^+$.

N-(6-Chloro-pyridin-3-yl)-4-hydroxyamino-benzamide (38): dec 200° C.; $^1$H NMR (300 MHz, DMSO-d$_6$) δ10.24 (1H, brs), 8.86 (1H, s), 8.75 (1H, d, J=2.4 Hz), 8.61 (1H, s), 8.22 (1H, dd, J=8.7, 2.8 Hz), 7.83 (2H, d, J=8.5 Hz) and 7.47 (1H, d, J=8.7 Hz); MS (ESI) m/z: 261.9 [M–H]$^+$.

N-(6-Chloro-pyridin-3-yl)-3-fluoro-4-hydroxyamino-benzamide (39): $^1$H NMR (300 MHz, DMSO-d$_6$) δ10.16 (1H, brs), 8.74 (1H, d, J=2.6 Hz), 8.19 (1H, dt, J=8.7, 2.8 Hz), 7.66 (1H, dd, J=12.7, 1.7 Hz), 7.60 (1H, d, J=8.4 Hz), 7.47 (1H, d, J=8.7 Hz), 6.80 (1H, t, J=8.9 Hz) and 5.93 (2H, brs); MS (ESI) m/z: 280.0 [M–H]$^+$.

N-(6-Chloro-pyridin-3-yl)-4-methylsulfamoyl-benzamide (40): mp 186–189° C.; $^1$H NMR (300 MHz, DMSO-d$_6$) δ10.78 (1H, brs), 8.77 (1H, d, J=2.3 Hz), 8.23 (1H, dt, J=8.7, 2.8 Hz), 8.13 (2H, d, J=8.4 Hz), 7.99 (1H, d, J=8.2 Hz), 7.63 (1H, q, J=5.2 Hz), 7.53 (1H, d, J=8.7 Hz) and 2.43 (3H, s); MS (ESI) m/z: 326.2 [M+H]$^+$.

4-Amino-N-(6-chloro-pyridin-3-yl)-3-fluoro-benzamide (41): mp 193° C.; $^1$H NMR (300 MHz, DMSO-d$_6$) δ10.16 (1H, brs), 8.73 (1H, d, J=2.6 Hz), 8.20 (1H, dd, J=8.7, 2.8 Hz), 7.66 (1H, dd, J=12.7, 1.7 Hz), 7.59 (1H, dd, J=8.4, 1.9 Hz), 7.46 (1H, d, J=8.7 Hz), 6.80 (1H, t, J=8.7 Hz) and 5.94 (2H, s); MS (ESI) m/z: 266.0 [M+H]$^+$.

N-(6-Chloro-pyridin-3-yl)-4-nitro-benzamide (42): mp 193° C.; $^1$H NMR (300 MHz, DMSO-d$_6$) δ10.88 (1H, brs), 8.77 (1H, d, J=2.3 Hz), 8.39 (1H, s), 8.36 (1H, s), 8.23 (1H, dt, J=8.7, 2.8 Hz), 8.20 (1H, s), 8.17 (1H, s), 7.63 (1H, q, J=5.2 Hz) and 7.54 (1H, d, J=8.7 Hz): MS (ESI) m/z: 275.9 [M+H]$^+$.

N-(6-Chloro-pyridin-3-yl)-3-chloro-4-fluoro-benzamide (43): mp 173° C.; $^1$H NMR (300 MHz, DMSO-d$_6$) δ10.65 (1H, brs), 8.74 (1H, s), 8.23–8.18 (2H, m), 8.01–7.97 (1H, m), 7.61 (1H, t, J=9.1 Hz) and 7.52 (1H, d, J=8.7 Hz): MS (ESI) m/z: 285.0 [M+H]$^+$.

EXAMPLE 9

This example illustrates a KCNQ2 screening protocol for evaluating compounds of the present invention.

Cells expressing voltage-gated K$^+$ channels, such as KCNQ2-like channels were loaded with $^{86}$Rb$^+$ by culture in media containing $^{86}$RbCl. Following loading, culture media was removed and the cells were washed in EBSS to remove residual traces of $^{86}$Rb$^+$. Cells were preincubated with drug (0.01–30 μM in EBSS) and then $^{86}$Rb$^+$ efflux was stimulated by exposing cells to EBSS solution supplemented with a sub-maximal concentration of KCl (generally 7–20 mM) in the continued presence of drug. After a suitable efflux period, the EBSS/KCl solution was removed from the cells and the $^{86}$Rb$^+$ content determined by Cherenkov counting (Wallac Trilux). Cells were then lysed with a SDS solution and the $^{86}$Rb$^+$ content of the lysate determined. Percent $^{86}$Rb$^+$ efflux was calculated according to:

($^{86}$Rb$^+$ content in EBSS/($^{86}$Rb$^+$ content in EBSS+$^{86}$Rb$^+$ content of the lysate))*100

Efflux was normalized to the maximal $^{86}$Rb$^+$ efflux (i.e., that induced by a high concentration of KCl, generally 30–135 mM).

Compounds 1–43 (FIG. 1) were prepared according to the general methods set forth in the examples and they were assayed using the above-described method. The activity of the assayed compounds ranged from about 30% to greater than about 70% efflux.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of increasing ion flow through voltage-dependent potassium channels in a cell, said method comprising contacting said cell with a potassium channel-opening amount of a compound of the formula:

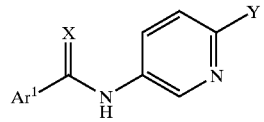

wherein,
- $Ar^1$ is a substituted or unsubstituted heteroaryl group selected from indolyl, substituted indolyl, benzofuranyl, substituted benzofuranyl, furanyl, substituted furanyl, thienyl, substituted thienyl, isothiazolyl, substituted isothiazolyl, pyrazolyl, and substituted pyrazolyl and substituted phenyl
- such that when $Ar^1$ is substituted heteroaryl it bears a substituent which is selected from halogen, alkyl, halo($C_1$–$C_4$)alkyl, ($C_1$–$C_4$)alkoxy, halo($C_1$–$C_4$)alkoxy, nitro, cyano, —$NR^7C(O)R^8$, —$NR^7R^8$, phenyl and substituted phenyl, and
- when $Ar^1$ is substituted phenyl it bears a substituent which is selected from halogen, alkyl, halo($C_1$–$C_4$)alkyl, ($C_1$–$C_4$)alkoxy, halo($C_1$–$C_4$)alkoxy, nitro, cyano, —$NR^7R^8$, phenyl and substituted phenyl, wherein
  - $R^7$ and $R^8$ are members independently selected from the group consisting of hydrogen, ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl($C_1$–$C_4$)alkyl, or $R^7$ and $R^8$ taken together with the nitrogen to which each is attached form a 5-, 6- or 7-membered ring optionally having additional heteroatoms at the ring vertices;
- X is a member selected from the group consisting of O, S and N-$R^1$, wherein,
  - $R^1$ is a member selected from the group consisting of H, ($C_1$–$C_8$)alkyl, substituted ($C_1$–$C_8$)alkyl, heteroalkyl, substituted heteroalkyl, aryl, substituted aryl, heteroaryl, substituted heteroaryl, aryl($C_1$–$C_4$)alkyl, substituted aryl($C_1$–$C_4$)alkyl, CN, —C(O)R2, —OR3, —C(O)NR$^3$R$^4$, and —S(O)$_2$NR$^3$R$^4$, wherein,
    - $R^2$ is a member selected from the group consisting of ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, alkaryl, substituted aryl, heteroaryl, substituted heteroaryl, aryl($C_1$–$C_4$)alkyl and substituted aryl($C_1$–$C_4$)alkyl;
    - $R^3$ and $R^4$ are each members independently selected from the group consisting of hydrogen, ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl($C_1$–$C_4$)alkyl, or $R^3$ and $R^4$ can be combined with the nitrogen to which each is attached to form a 5-, 6- or 7-membered ring optionally having additional heteroatoms at the ring vertices; and
- Y is a member selected from the group consisting of halogen, $C_1$–$C_4$ alkyl, $C_1$–$C_4$ substituted alkyl, —$OCH_3$ and —$OCF_3$.

2. The method according to claim 1, wherein X is O.

3. The method according to claim 1, wherein $Ar^1$ is a member selected from the group consisting of substituted or unsubstituted 2-indolyl and substituted or unsubstituted 2-thienyl.

4. The method according to claim 1, wherein said voltage-dependent potassium channel is responsible for the M-current.

5. The method according to claim 1, wherein said voltage-dependent potassium channel comprises KCNQ subunits.

6. A method of increasing ion flow through voltage-dependent potassium channels in a cell, said method comprising contacting said cell with a potassium channel-opening amount of a compound of the formula:

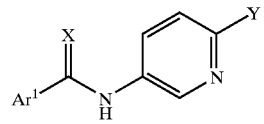

wherein,
- $Ar^1$ is substituted phenyl bearing a substituent —NC(O)$R^7R^8$, wherein
  - $R^7$ and $R^8$ are members independently selected from the group consisting of hydrogen, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl($C_1$–$C_4$)alkyl, or $^7$ and $R^8$ taken together with the nitrogen to which each is attached form a 5-, 6- or 7-membered ring optionally having additional heteroatoms at the ring vertices;
- X is a member selected from the group consisting of O, S and N-$R^1$, wherein,
  - $R^1$ is a member selected from the group consisting of H, ($C_1$–$C_8$)alkyl, substituted ($C_1$–$C_8$)alkyl, heteroalkyl, substituted heteroalkyl, aryl, substituted aryl, heteroaryl, substituted heteroaryl, aryl($C_1$–$C_4$) alkyl, substituted aryl($C_1$–$C_4$)alkyl, CN, —C(O)$R^2$, —$OR^3$, —C(O)NR$^3$R$^4$, and —S(O)$_2$NR$^3$R$^4$, wherein,
    - $R^2$ is a member selected from the group consisting of ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, alkaryl, substituted aryl, heteroaryl, substituted heteroaryl, aryl($C_1$–$C_4$)alkyl and substituted aryl($C_1$–$C_4$)alkyl;
    - $R^3$ and $R^4$ are each members independently selected from the group consisting of hydrogen, ($C_1$–$C_8$) alkyl, substituted $C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl($C_1$–$C_4$)alkyl, or $R^3$ and $R^4$ can be combined with the nitrogen to which each is attached to form a 5-, 6- or 7-membered ring optionally having additional heteroatoms at the ring vertices; and
- Y is a member selected from the group consisting of halogen, $C_1$–$C_4$ alkyl, $C_1$–$C_4$ substituted alkyl, —$OCH_3$ and —$OCF_3$.

7. The method according to claim 6, wherein said voltage-dependent potassium channel is responsible for the M-current.

8. The method according to claim 6, wherein said voltage-dependent potassium channel comprises KCNQ subunits.

9. A method of increasing ion flow through voltage-dependent potassium channels in a cell, said method comprising contacting said cell with a potassium channel-opening amount of a compound of the formula:

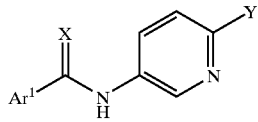

wherein,

Ar$^1$ is substituted or unsubstituted multiple ring aryl, wherein Ar$^1$ substituents are members selected from the group consisting of halogen, alkyl, halo($C_1$-$C_4$)alkyl, ($C_1$-$C_4$)alkoxy, halo($C_1$-$C_4$)alkoxy, nitro, cyano, —NR$^7$C(O)R$^8$, —NR$^7$R$^8$, phenyl and substituted phenyl, R$^7$ and R$^8$ are members independently selected from the group consisting of hydrogen, ($C_1$-$C_8$)alkyl, substituted ($C_1$-$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$-$C_4$)alkyl and substituted aryl($C_1$-$C_4$)alkyl, or R$^7$ and R$^8$ taken together with the nitrogen to which each is attached form a 5-, 6- or 7-membered ring optionally having additional heteroatoms at the ring vertices;

X is a member selected from the group consisting of O, S and N—R$^1$, wherein,

R$^1$ is a member selected from the group consisting of H, ($C_1$-$C_8$)alkyl, substituted ($C_1$-$C_8$)alkyl, heteroalkyl, substituted heteroalkyl, aryl, substituted aryl, heteroaryl, substituted heteroaryl, aryl($C_1$-$C_4$)alkyl, substituted aryl($C_1$-$C_4$)alkyl, CN, —C(O)R$^2$, —OR$^3$, —C(O)NR$^3$R$^4$, and —S(O)$_2$NR$^3$R$^4$, wherein, R$^2$ is a member selected from the group consisting of ($C_1$-$C_8$)alkyl, substituted ($C_1$-$C_8$)alkyl, cycloalkyl, substituted cycloalkyl, heteroalkyl, substituted heteroalkyl, heterocyclyl, substituted heterocyclyl, alkaryl, substituted aryl, heteroaryl, substituted heteroaryl, aryl($C_1$-$C_4$)alkyl and substituted aryl($C_1$-$C_4$)alkyl;

R$^3$ and R$^4$ are each members independently selected from the group consisting of hydrogen, ($C_1$-$C_8$) alkyl, substituted ($C_1$-$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$-$C_4$)alkyl and substituted aryl($C_1$-$C_4$alkyl, or R$^3$ and R$^4$ can be combined with the nitrogen to which each is attached to form a 5-, 6- or 7-membered ring optionally having additional heteroatoms at the ring vertices; and Y is a member selected from the group consisting of halogen, $C_1$-$C_4$ alkyl, $C_1$-$C_4$ substituted alkyl, —OCH$_3$ and —OCF$_3$.

10. The method according to claim 9, wherein said voltage-dependent potassium channel is responsible for the M-current.

11. The method according to claim 9, wherein said voltage-dependent potassium channel comprises KCNQ subunits.

12. A method of increasing ion flow through voltage-dependent potassium channels in a cell, said method comprising contacting said cell with a potassium channel-opening amount of a compound of the formula:

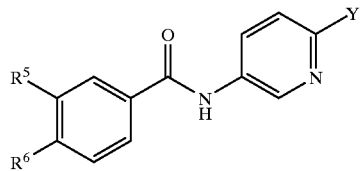

wherein,

Y is a member selected from the group consisting of halogen, $C_1$-$C_4$ alkyl, $C_1$-$C_4$ substituted alkyl, —OCH$_3$ and —OCF$_3$; and R$^5$ and R$^6$ are members independently selected from the group consisting of H, halogen, substituted or unsubstituted alkyl, halo($C_1$-$C_4$)alkyl, nitro, cyano and substituted or unsubstituted phenyl, with the proviso that both R$^5$ and R$^6$ are not H.

13. The method according to claim 12, wherein R$^5$ and R$^6$ are members independently selected from the group consisting of H, F, and Cl, with the proviso that both R$^5$ and R$^6$ are not H.

14. The method according to claim 12, wherein said voltage-dependent potassium channel is responsible for the M-current.

15. The method according to claim 12, wherein said voltage-dependent potassium channel comprises KCNQ subunits.

16. A method of increasing ion flow through voltage-dependent potassium channels in a cell, said method comprising contacting said cell with a potassium channel-opening amount of a compound of the formula:

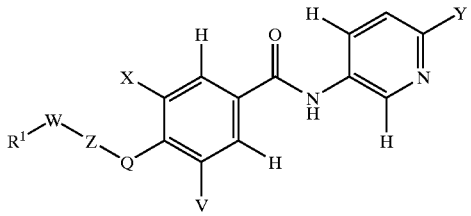

wherein Y is a member selected from H, methyl, methoxy, trifluoromethoxy, —CF$_3$ or halo;

V and X are members independently selected from H, halo, substituted or unsubstituted lower alkyl, R$^1$ is a member independently selected from substituted or unsubstituted lower alkyl, substituted or unsubstituted lower heteroalkyl, substituted or unsubstituted carbocycle, substituted or unsubstituted heterocycle, substituted or unsubstituted aryl, or substituted or unsubstituted heteroary;

Q and W are members independently selected from —(CR$^2$R$^3$)$_t$—(CH$_2$)$_n$—, —(CH$_2$)$_n$—(CR$^2$R$^3$)$_t$, —C(R$^4$)═C(R$^5$)—, and —C≡C—wherein R$^2$ and R$^3$ are members independently selected from H, F, substituted or unsubstituted lower alkyl or substituted or unsubstituted lower heteroalkyl, in which R$^2$ and R$^3$ are optionally joined to form a cyclic structure which is a member selected from the group consisting of cycloalkyl and heterocycle groups, or $R^2$ and $R^3$ together with the carbon to which they are attached form —C(O)—;

Z is a member selected from —O—, $S(O)_m$—, —N($R^4$)—, —N($R^4$)C(O)—, —C(O)N($R^4$)—, —C(O)—, —N($R^4$)C(O)N($R^5$)—, —N($R^4$)C(O)O—, $(CR^2R^3)_p$, and —$SO_2$N($R^4$)—, wherein
$R^4$ and $R^5$ are members independently selected from the group consisting of H, substituted or unsubstituted lower alkyl, substituted or unsubstituted lower heteroalkyl, substituted or unsubstituted aryl, or substituted or unsubstituted heteroaryl, in which $R^1$ is optionally joined together with either X or $R^4$ to form a substituted or unsubstituted heterocycle;
m is an integer from 0 to 2, inclusive;
n is an integer from 0 to 3, inclusive; and
t is an integer from 0 to 2, inclusive.

17. The method according to claim 16, wherein Y is a member selected from chloro and methyl.

18. The method according to claim 16, wherein Z is a member selected from the group consisting of —S—, $SO_2$—, —$(CR^2R^3)_t$—, and —O—.

19. The method according to claim 16, wherein $R^4$ is H.

20. The method according to claim 16, wherein $R^1$ is a member selected from the group consisting of:

[structures]

21. The method according to claim 16, wherein n is an integer from 0 to 2, inclusive; and t is an integer from 0 to 1, inclusive.

22. The method according to claim 16, wherein said compound has a structure which is a member selected from the group consisting of the compounds set forth in FIG. 1.

23. The method according to claim 16, wherein said compound has the structure:

[structure]

wherein
$R^1$—W—Z—Q— is $R^6$, and $R^6$ is selected from the group consisting of H, halogen, substituted or unsubstituted alkyl, halo($C_1$–$C_4$)alkyl, nitro, cyano, substituted or unsubstituted phenyl, $R^9$O—; $R^9$S—; $R^9$NH—; $R^9$NH—; $R^9$NHS(O)$_2$—; $R^9$S(O)$_2$—, with the proviso that both X and $R^6$ are not H;
wherein $R^9$ is a member selected from aryl, and alkylaryl, when there is more than one group per molecule, each $R^9$ group is independently selected; and
Y is a member selected from halogen, $C_1$–$C_4$ alkyl, —OCH$_3$, and —OCF$_3$.

24. The method according to claim 23, wherein the alkyl component of said alkylaryl group is a $C_1$–$C_4$ alkyl group.

25. The method according to claim 23, wherein said aryl group of $R^9$ is heteroaryl.

26. The method according to claim 23, wherein the aryl component of said ($C_1$–$C_4$)alkylaryl group is a substituted or unsubstituted aryl group.

27. The method according to claim 23, wherein the aryl component of said ($C_1$–$C_4$)alkylaryl group is a substituted or unsubstituted heteroaryl group.

28. The method according to claim 16, wherein said voltage-dependent potassium channel is responsible for the M-current.

29. The method according to claim 16, wherein said voltage-dependent potassium channel comprises KCNQ subunits.

30. A method of treating a central or peripheral nervous system disorder or condition through modulation of a voltage-dependent potassium channel, said method comprising administering to a subject in need of such treatment, an effective amount of a compound having the formula:

[structure]

wherein,
Ar$^1$ is a substituted or unsubstituted heteroaryl group selected from indolyl, substituted indolyl, benzofuranyl, substituted benzofuranyl, furanyl, substituted furanyl, thienyl, substituted thienyl, isothiazolyl, substituted isothiazolyl, pyrazolyl, and substituted pyrazolyl and substituted phenyl
such that when Ar$^1$ is substituted heteroaryl it bears a substituent which is selected from halogen, alkyl, halo ($C_1$–$C_4$)alkyl, ($C_1$–$C_4$)alkoxy, halo($C_1$–$C_4$)alkoxy, nitro, cyano, —NR$^7$C(O)R$^8$, —NR$^7$R$^8$, phenyl and substituted phenyl, and when Ar¹ is substituted phenyl it bears a substituent which is selected from halogen, alkyl, halo($C_1$–$C_4$)alkyl, ($C_1$–$C_4$)alkoxy, halo($C_1$–$C_4$)alkoxy, nitro, cyano, —NR⁷R⁸, phenyl and substituted phenyl, wherein R⁷ and R⁸ are members independently selected from the group consisting of hydrogen, ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl($C_1$–$C_4$)alkyl, or R⁷ and R⁸ taken together with the nitrogen to which each is attached form a 5-, 6- or 7-membered ring optionally having additional heteroatoms at the ring vertices;

X is a member selected from the group consisting of O, S and N-R¹, wherein,

R¹ is a member selected from the group consisting of H, ($C_1$–$C_8$)alkyl, substituted ($C_1$–$C_8$)alkyl, heteroalkyl, substituted heteroalkyl, aryl, substituted aryl, heteroaryl, substituted heteroaryl, aryl($C_1$–$C_4$)alkyl, substituted aryl($C_1$–$C_4$)alkyl, CN, —C(O)R², —OR³, —C(O)NR³R⁴, and —S(O)₂NR³R⁴,
wherein, R¹ is a member selected from the group consisting of ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, alkaryl, substituted aryl, heteroaryl, substituted heteroaryl, aryl($C_1$–$C_4$)alkyl and substituted aryl($C_1$–$C_4$)alkyl;

R³ and R⁴ are each members independently selected from the group consisting of hydrogen, ($C_1$–$C_8$) alkyl, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl($C_1$–$C_4$)alkyl, or R³ and R⁴ can be combined with the nitrogen to which each is attached to form a 5-, 6- or 7-membered ring optionally having additional heteroatoms at the ring vertices; and Y is a member selected from the group consisting of halogen, $C_1$–$C_4$ alkyl, $C_1$–$C_4$ substituted alkyl, —OCH₃ and —OCF₃.

31. The method according to claim 30, wherein X is O.

32. The method according to claim 30, wherein Ar¹ is a member selected from the group consisting of substituted or unsubstituted 2-indolyl and substituted or unsubstituted 2-thienyl.

33. The method according to claim 30, wherein said disorder or condition is selected from the group consisting of migraine, ataxia, Parkinson's disease, bipolar disorders, spasticity, mood disorders, brain tumors, psychotic disorders, myokymia, seizures, epilepsy, hearing loss, vision loss, Alzheimer's disease, age-related memory loss, learning deficiencies, motor neuron diseases, and stroke.

34. The method according to claim 30, wherein said disorder or condition is hearing loss.

35. The method according to claim 30, wherein said disorder or condition is epilepsy or seizures.

36. A method of treating a central or peripheral nervous system disorder or condition through modulation of a voltage-dependent potassium channel, said method comprising administering to a subject in need of such treatment, an effective amount of a compound having the formula:

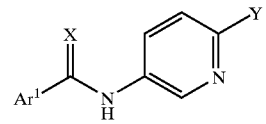

wherein,

Ar¹ is substituted phenyl bearing a substituent —NC(O) R⁷R⁸, wherein

R⁷ and R⁸ are members independently selected from the group consisting of hydrogen, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl($C_1$–$C_4$)alkyl, or R⁷ and R⁸ taken together with the nitrogen to which each is attached form a 5-, 6- or 7-membered ring optionally having additional heteroatoms at the ring vertices;

X is a member selected from the group consisting of O, S and N-R¹, wherein,

R¹ is a member selected from the group consisting of H, ($C_1$–$C_8$)alkyl, substituted ($C_1$–$C_8$)alkyl, heteroalkyl, substituted heteroalkyl, aryl, substituted aryl, heteroaryl, substituted heteroaryl, aryl($C_1$–$C_4$) alkyl, substituted aryl($C_1$–$C_4$)alkyl, CN, —C(O)R², —OR³, —C(O)NR³R⁴, and —S(O)₂NR³R⁴,
wherein, R¹ is a member selected from the group consisting of ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, alkaryl, substituted aryl, heteroaryl, substituted heteroaryl, aryl($C_1$–$C_4$alkyl and substituted aryl($C_1$–$C_4$)alkyl;

R³ and R⁴ are each members independently selected from the group consisting of hydrogen, ($C_1$–$C_8$) alkyl, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$)alkyl and substituted aryl($C_1$–$C_4$)alkyl, or R³ and R⁴ can be combined with the nitrogen to which each is attached to form a 5-, 6- or 7-membered ring optionally having additional heteroatoms at the ring vertices; and Y is a member selected from the group consisting of halogen, $C_1$–$C_4$ alkyl, $C_1$–$C_4$ substituted alkyl, —OCH₃ and —OCF₃.

37. The method according to claim 36, wherein said disorder or condition is selected from the group consisting of migraine, ataxia, Parkinson's disease, bipolar disorders, spasticity, mood disorders, brain tumors, psychotic disorders, myokymia, seizures, epilepsy, hearing loss, vision loss, Alzheimer's disease, age-related memory loss, learning deficiencies, motor neuron diseases, and stroke.

38. The method according to claim 36, wherein said disorder or condition is hearing loss.

39. The method according to claim 36, wherein said disorder or condition is epilepsy or seizures.

40. A method of treating a central or peripheral nervous system disorder or condition through modulation of a voltage-dependent potassium channel, said method comprising administering to a subject in need of such treatment, an effective amount of a compound having the formula:

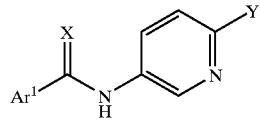

wherein,
Ar$^1$ is substituted or unsubstituted multiple ring aryl, wherein Ar$^1$ substituents are members selected from the group consisting of halogen, alkyl, halo(C$_1$–C$_4$)alkyl, (C$_1$–C$_4$)alkoxy, halo(C$_1$–C$_4$)alkoxy, nitro, cyano, —NR$^7$C(O)R$^8$, —NR$^7$R$^8$, phenyl and substituted phenyl, R$^7$ and R$^8$ are members independently selected from the group consisting of hydrogen, (C$_1$–C$_8$)alkyl, substituted (C$_1$–C$_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl (C$_1$–C$_4$)alkyl and substituted aryl(C$_1$–C$_4$)alkyl, or R$^7$ and R$^8$ taken together with the nitrogen to which each is attached form a 5-, 6- or 7-membered ring optionally having additional hetero atoms at the ring vertices;

X is a member selected from the group consisting of O, S and N-R$^1$, wherein,
R$^1$ is a member selected from the group consisting of H, (C$_1$–C$_8$)alkyl, substituted (C$_1$–C$_8$)alkyl, heteroalkyl, substituted heteroalkyl, aryl, substituted aryl, heteroaryl, substituted heteroaryl, aryl(C$_1$–C$_4$) alkyl, substituted aryl(C$_1$–C$_4$)alkyl, CN, —C(O)R$^2$, —OR$^3$, —C(O)NR$^3$R$^4$, and —S(O)$_2$NR$^3$R$^4$, wherein,
R$^2$ is a member selected from the group consisting of (C$_1$–C$_8$)alkyl, substituted (C$_1$–C$_8$)alkyl, cycloalkyl, substituted cycloalkyl, heteroalkyl, substituted heteroalkyl, heterocyclyl, substituted heterocyclyl, alkaryl, substituted aryl, heteroaryl, substituted heteroaryl, aryl(C$_1$–C$_4$)alkyl and substituted aryl(C$_1$–C$_4$)alkyl;
R$^3$ and R$^4$ are each members independently selected from the group consisting of hydrogen, (C$_1$–C$_8$) alkyl, substituted (C$_1$–C$_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl(C$_1$–C$_4$)alkyl and substituted aryl(C$_1$–C$_4$)alkyl, or R$^3$ and R$^4$ can be combined with the nitrogen to which each is attached to form a 5-, 6- or 7-membered ring optionally having additional heteroatoms at the ring vertices; and Y is a member selected from the group consisting of halogen, C$_1$–C$_4$ alkyl, C$_1$–C$_4$ substituted alkyl, —OCH$_3$ and —OCF$_3$.

41. The method according to claim 40, wherein said disorder or condition is selected from the group consisting of migraine, ataxia, Parkinson's disease, bipolar disorders, spasticity, mood disorders, brain tumors, psychotic disorders, myokymia, seizures, epilepsy, hearing loss, vision loss, Alzheimer's disease, age-related memory loss, learning deficiencies, motor neuron diseases, and stroke.

42. The method according to claim 40, wherein said disorder or condition is hearing loss.

43. The method according to claim 40, wherein said disorder or condition is epilepsy or seizures.

44. A method of treating a central or peripheral nervous system disorder or condition through modulation of a voltage-dependent potassium channel, said method comprising administering to a subject in need of such treatment, an effective amount of a compound having the formula:

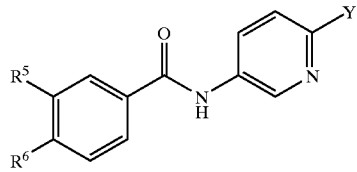

wherein,
Y is a member selected from the group consisting of halogen, C$_1$–C$_4$ alkyl, C$_1$–C$_4$ substituted alkyl, —OCH$_3$ and —OCF$_3$; and
R$^5$ and R$^6$ are members independently selected from the group consisting of H, halogen, substituted or unsubstituted alkyl, halo(C$_1$–C$_4$)alkyl, nitro, cyano and substituted or unsubstituted phenyl, with the proviso that both R$^5$ and R$^6$ are not H.

45. The method according to claim 44, wherein said disorder or condition is selected from the group consisting of migraine, ataxia, Parkinson's disease, bipolar disorders, spasticity, mood disorders, brain tumors, psychotic disorders, myokymia, seizures, epilepsy, hearing loss, vision loss, Alzheimer's disease, age-related memory loss, learning deficiencies, motor neuron diseases, and stroke.

46. The method according to claim 44, wherein said disorder or condition is hearing loss.

47. The method according to claim 44, wherein said disorder or condition is epilepsy or seizures.

48. A method of treating a central or peripheral nervous system disorder or condition through modulation of a voltage-dependent potassium channel, said method comprising administering to a subject in need of such treatment, an effective amount of a compound having the formula:

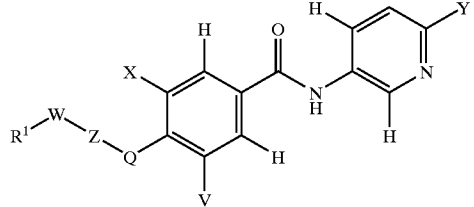

wherein Y is a member selected from H, methyl, methoxy, trifluoromethoxy, —CF$_3$ or halo;
V and X are members independently selected from H, halo, substituted or unsubstituted lower alkyl,
R$^1$, R$^{11}$, R$^{12}$ and R$^{13}$ are members R$^1$ is a member independently selected from substituted or unsubstituted lower alkyl, substituted or unsubstituted lower heteroalkyl, substituted or unsubstituted carbocycle, substituted or unsubstituted heterocycle, substituted or unsubstituted aryl, or substituted or unsubstituted heteroary;
Q and W are members independently selected from —(CR$^2$R$^3$)$_1$—(CH$_2$)$_n$—, —(CH$_2$)$_n$—(CR$^2$R$^3$)$_t$, —C(R$^4$)=C(R$^5$)—, and —C≡C— wherein R$^2$ and R$^3$ are members independently selected from H, F, substituted or unsubstituted lower alkyl or substituted or unsubstituted lower heteroalkyl, in which R$^2$ and R$^3$ are optionally joined to form a cyclic structure which is a member selected from the group consisting of cycloalkyl and heterocycle groups, or R² and R³ together with the carbon to which they are attached form —C(O)—;

Z is a member selected from —O—, —S(O)m—, N(R⁴)—, —N(R⁴)C(O)—, —C(O)N(R⁴)—, —C(O)—, —N(R⁴)C(O)N(R⁵)—, —N(R⁴)C(O)O—, (CR²R³)ₚ, and —SO₂N(R⁴)—, wherein R⁴ and R⁵ are members independently selected from the group consisting of H, substituted or unsubstituted lower alkyl, substituted or unsubstituted lower heteroalkyl, substituted or unsubstituted aryl, or substituted or unsubstituted heteroaryl, in which R¹ is optionally joined together with either X or R⁴ to form a substituted or unsubstituted heterocycle;

m is an integer from 0 to 2, inclusive;
n is an integer from 0 to 3, inclusive; and
t is an integer from 0 to 2, inclusive.

49. The method according to claim 48, wherein Y is a member selected from chloro and methyl.

50. The method according to claim 48, wherein Z is a member selected from the group consisting of —S—, SO₂—, —(CR²R³)ₜ—, and —O—.

51. The method according to claims 48, wherein R⁴ is H.

52. The method according to claim 48, wherein R¹ is a member selected from the group consisting of:

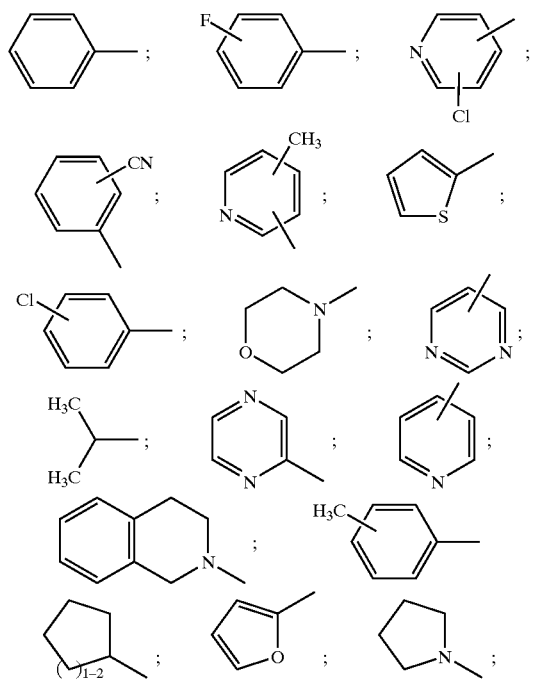

-continued

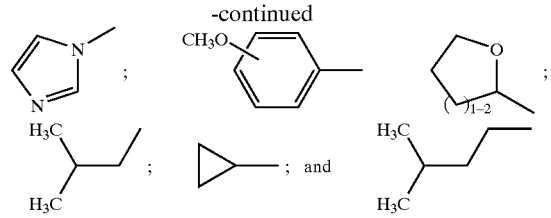

53. The method according to claim 48, wherein n is an integer from 0 to 2, inclusive; and t is an integer from 0 to 1, inclusive.

54. The method according to claims 48, wherein said compound has a structure which is a member selected from the group consisting of the compounds set forth in FIG. 1.

55. The method according to claim 48, wherein said compound has the structure:

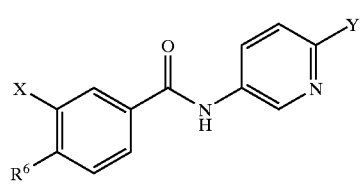

wherein

R¹—W—Z—Q— is R⁶, and R⁶ is selected from the group consisting of H, halogen, substituted or unsubstituted alkyl, halo(C₁–C₄)alkyl, nitro, cyano, substituted or unsubstituted phenyl, R⁹O—; R⁹S—; R⁹NH—; R⁹NH—; R⁹NHS(O)₂—; R⁹S(O)₂—, with the proviso that both X and R⁶ are not H; wherein R⁹ is a member selected from aryl, and alkylaryl, when there is more than one R⁹ group per molecule, each R⁹ group is independently selected; and Y is a member selected from halogen, C₁–C₄ alkyl, —OCH₃, and —OCF₃.

56. The method according to claim 55, wherein the alkyl component of said alkylaryl group is a C₁–C₄ alkyl group.

57. The method according to claim 55, wherein said aryl group of R⁹ is heteroaryl.

58. The method according to claim 55, wherein the aryl component of said (C₁–C₄)alkylaryl group is a substituted or unsubstituted aryl group.

59. The method according to claim 55, wherein the aryl component of said (C₁–C₄)alkylaryl group is a substituted or unsubstituted heteroaryl group.

* * * * *

UNITED STATES PATENT AND TRADEMARK OFFICE
CERTIFICATE OF CORRECTION

PATENT NO.    : 6,737,422 B2
DATED         : May 18, 2004
INVENTOR(S)   : McNaughton-Smith et al.

It is certified that error appears in the above-identified patent and that said Letters Patent is hereby corrected as shown below:

Column 29,
Line 46, replace "–C(O) R2" with -- –C(O) $R^2$ --.
Line 47, replace "–OR3", with -- –$OR^3$ --.

Column 30,
Line 33, replace ""7"" with -- $R^7$ --.
Line 55, replace "$C_1$-$C_8$)" with -- ($C_1$-$C_8$) --.

Column 31,
Line 57, replace "($C_1$-$C_4$alkyl" with -- ($C_1$-$C_4$)alkyl --.

Column 32,
Line 54, after "alkyl", replace ", $R^1$" with -- ; -- and start a new paragraph with -- $R^1$ is a --.
Line 54, after "alkyl" insert -- and $CF_3$; --.
Line 60, replace "heteroary;" with -- heteroaryl; --.

Column 34,
Line 21, after "one" insert -- $R^9$ --.

Column 35,
Line 25, replace "$R^1$" with -- $R^2$ --.
Line 50, replace ""2-indolyl" with -- 2-indolyl --.
Line 51, replace ""2-thienyl" with -- 2-thienyl --.

Column 36,
Line 30, replace "$R^1$" with -- $R^2$ --.
Line 35, replace "($C_1$-$C_4$alkyl" with -- ($C_1$-$C_4$)alkyl --.

UNITED STATES PATENT AND TRADEMARK OFFICE
CERTIFICATE OF CORRECTION

PATENT NO. : 6,737,422 B2
DATED : May 18, 2004
INVENTOR(S) : McNaughton-Smith et al.

It is certified that error appears in the above-identified patent and that said Letters Patent is hereby corrected as shown below:

Column 38,
Line 54, after "alkyl" insert -- and $CF_3$; --.
Line 55, delete "$R^1$, $R^{11}$, $R^{12}$ and $R^{13}$ are members".
Line 61, replace "eroary;" with -- eroaryl; --.

Column 39,
Line 6, replace "-S(O)m" with -- $S(O)_m$ --.

Signed and Sealed this

Twelfth Day of October, 2004

JON W. DUDAS
*Director of the United States Patent and Trademark Office*